(12) United States Patent
Steward, Jr. et al.

(10) Patent No.: US 8,573,844 B2
(45) Date of Patent: *Nov. 5, 2013

(54) ADJUSTABLE DENTAL X-RAY IMAGE MEDIA HOLDER

(75) Inventors: Curtis L. Steward, Jr., Sandwich, IL (US); Paul McDonough, Woodstock, IL (US); Thaddeus J. Hartlaub, Sheboygan, WI (US)

(73) Assignee: DENTSPLY International Inc., York, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/884,585

(22) Filed: Sep. 17, 2010

(65) Prior Publication Data

US 2011/0164733 A1 Jul. 7, 2011

Related U.S. Application Data

(63) Continuation-in-part of application No. 11/980,836, filed on Oct. 31, 2007, now Pat. No. 7,959,354, and a continuation-in-part of application No. 11/807,413, filed on May 29, 2007, now abandoned.

(60) Provisional application No. 60/809,491, filed on May 30, 2006.

(51) Int. Cl.
*G03B 42/02* (2006.01)

(52) U.S. Cl.
USPC ............................................ 378/170; 378/168

(58) Field of Classification Search
USPC .......... 378/167, 168, 170, 181, 182, 183, 184
See application file for complete search history.

(56) References Cited

U.S. PATENT DOCUMENTS

| | | |
|---|---|---|
| 1,012,561 A | 12/1911 | Ketcham |
| 3,473,026 A | 10/1969 | Undergrove |
| 4,554,676 A | 11/1985 | Maldonado et al. |
| 4,866,750 A | 9/1989 | Chavarria et al. |
| 4,941,164 A | 7/1990 | Schuller et al. |
| 5,090,047 A | 2/1992 | Angotti et al. |
| 5,119,410 A | 6/1992 | Donato |
| 5,256,982 A | 10/1993 | Willis |
| 5,289,522 A | 2/1994 | Kanbar et al. |

(Continued)

FOREIGN PATENT DOCUMENTS

| | | |
|---|---|---|
| EP | 0379611 A1 | 8/1990 |
| EP | 0397599 B1 | 3/1994 |

(Continued)

*Primary Examiner* — Hoon Song
*Assistant Examiner* — Danielle Fox
(74) *Attorney, Agent, or Firm* — David A. Zdurne; Douglas J. Hura; Leana Levin

(57) ABSTRACT

A dental x-ray image media holder comprising: a backing plate affixed to a bite block, the backing plate including a least one channel for receiving a post affixed to the bite block, such that the bite block can be selectively moved within the channels to orient the bite block in a predetermined position relative to the backing plate; and a plurality of indicia, such that at least one of the indicia is used to indicate a first position of the bite block relative to the backing plate, the first position being associated with a predetermined first dental imaging procedure; and a locking member configured to prevent rotational movement of the bite block along a post axis upon engagement of the locking member.

20 Claims, 27 Drawing Sheets

(56) References Cited

U.S. PATENT DOCUMENTS

| | | |
|---|---|---|
| 5,327,477 A | 7/1994 | Levy |
| 5,513,240 A | 4/1996 | Hausmann et al. |
| 5,625,666 A | 4/1997 | Willis |
| 5,629,972 A | 5/1997 | Hausmann et al. |
| 6,461,038 B2 | 10/2002 | Pellegrine et al. |
| 6,652,141 B1 | 11/2003 | Cianciosi |
| 6,905,244 B2 | 6/2005 | Kilcher et al. |
| 7,033,075 B2 | 4/2006 | Landis et al. |
| 7,036,985 B2 | 5/2006 | Puente et al. |
| 7,959,354 B2 * | 6/2011 | Steward et al. .............. 378/170 |
| 2004/0015176 A1 | 1/2004 | Cosman |
| 2004/0170253 A1 | 9/2004 | Landis et al. |
| 2004/0213382 A1 | 10/2004 | Andell et al. |
| 2005/0047550 A1 | 3/2005 | Yao et al. |
| 2005/0185767 A1 | 8/2005 | Puente et al. |
| 2005/0220272 A1 | 10/2005 | Glazer |

FOREIGN PATENT DOCUMENTS

| | | |
|---|---|---|
| WO | 8301564 A1 | 5/1983 |
| WO | 2004013691 A1 | 2/2004 |
| WO | 2007142925 A1 | 12/2007 |

* cited by examiner

ADJUSTABLE DENTAL X-RAY IMAGE MEDIA HOLDER

CLAIM OF PRIORITY

The present invention claims the benefit of the filing date of U.S. Continuation-in-Part application Ser. No 11/980,836 (filed Oct. 31, 2007), U.S. Non-Provisional application Ser. No. 11/807,413 (filed May 29, 2007), and US Provisional Application Ser. No. 60/809,491 (filed May 30, 2006), which are hereby incorporated by reference for all purposes.

TECHNICAL FIELD

The present invention is related to dental x-ray image media holders. More particularly the invention relates to a device for securing a dental x-ray image media including film, phosphor plates, digital sensors and the like, and holding it in place relative to the x-ray target during the x-ray procedure. Specifically the invention relates to a holder that can be selectively used to take a plurality of different x-rays using a plurality of different sizes, shapes or configurations of image media. The inventive device has a bite block moveably affixed to an image media backing plate. The backing plate may be provided with flexible straps to secure an image media to the backing plate.

BACKGROUND OF THE INVENTION

Dental professionals have employed x-ray imaging for many years. A traditional dental x-ray procedure includes exposing an x-ray film to x-ray energy after it has passed through the target site. The film is developed and an image of the target site is achieved. It has also long been known that in order to obtain a useful image, the dental x-ray film must be positioned relative to the target site in a predetermined and secure manner. Many numbers of x-ray film holders and positioning devices have been developed, including for example, that shown in U.S. Pat. No. 3,473,026 which is hereby incorporated by reference for background purposes.

More recently, many dental professionals have used digital x-ray sensors in place of traditional x-ray films. An example of such a sensor is shown for example in U.S. Pat. No. 6,652,141 which is hereby incorporated by reference for background disclosure of x-ray sensors. As with x-ray films, it is necessary for the x-ray sensor to be secured in a predetermined position during the x-ray imaging procedure. In a manner similar to the use of x-ray films, holding and positioning devices have been developed for x-ray sensors. Digital sensors often have attached electrical connection cords such that the digital sensor transfers data to a storage or display device such as a computer.

Another type of image media common in the dental industry is a phosphor imaging plate. The x-ray shot is stored onto the imaging plate which is later read by a scanning machine or the like and the data is transferred to a storage or display device, such as a computer.

These and other type of devices that receive dental x-rays for dental purposes are herein collectively referred to as dental x-ray imaging media, sensors, imagers or the like. Any such devices that are sensitive to such x-rays is within the scope of the invention. It will be appreciated from the above discussion that the different image media holders while all accomplishing similar purposes, that is, dental diagnostics and the like, all operate in different manners. It is also the fact that the image media themselves are different in shape, size and configuration. For example, traditional x-ray films are often manufactured inside an envelope before being used with a patient. Phosphor imaging plates are often very thin, not much thicker than a sheet of paper or two and are placed into a barrier envelope before being used in an x-ray procedure. Digital sensors tend to be fairly thick in respective comparison due to the internal energy sensing components required for such devices. It is envisioned that in the future, other type of dental imaging media will be developed using similar or perhaps completely different technologies. These all have at least some commonality in that they generally must fit within the oral cavity and they must be securely held in a desired location during the x-ray procedure.

Adding to the complexity of using different imaging media is that even within a common type of media different manufacturers often provide media products that while they accomplish the same task as other media, are of a different size, shape or configuration.

Of course, it is also known that different set-ups must often be used for taking an x-ray image of different parts of the oral cavity. For example, conventionally dental x-rays taken in the oral cavity include anterior vertical periapical, anterior horizontal periapical, posterior horizontal periapical, posterior vertical periapical, horizontal bite-wing, vertical bite-wing, left and right images and other similar x-ray positions.

It will be appreciated that given the large number of different imaging media of different sizes, shapes and configurations, and given that many different x-ray procedures may be required in the oral cavity which require varied positioning of the imaging media relative to the tooth or other target site, the imaging media holder will have a different configuration for each possible combination. This requires the dental practitioner to normally stock a large number of imaging media holders in order to be reasonably certain that a proper holder is available at any given time for an x-ray procedure. It takes time and effort to match holders to specific imaging media.

A need exists therefore for a universal dental x-ray imaging media holder that will securely affix different shapes, sizes and configurations of such imaging media. It would also be desirable if the same holder could be used to hold such different media in a selected location during an x-ray procedure and which can be used to take more than one type of x-ray by being positioned at different locations in the oral cavity. The present invention provides an adjustable holder that meets these desires.

SUMMARY OF THE INVENTION

In one aspect, the present invention is directed to a dental x-ray image media holder comprising: a backing plate affixed to a bite block, the backing plate including: a least one channel for receiving a post affixed to the bite block, such that the bite block can be selectively moved within the channels to orient the bite block in a predetermined position relative to the backing plate; and a plurality of indicia, such that at least one of the indicia is used to indicate a first position of the bite block relative to the backing plate, the first position being associated with a predetermined first dental imaging procedure; and a locking member configured to prevent rotational movement of the bite block along a post axis upon engagement of the locking member.

In another aspect, the present invention is directed to a dental x-ray image media holder comprising: a backing plate affixed to a bite block, the backing plate including: a first side; a perimeter edge extending along the perimeter of the first side; at least one channel extending at least partially through the first side of the backing plate for receiving a post affixed to the bite block, such that the bite block can be selectively moved within the channel to orient the bite block in a predetermined position relative to the backing plate; and a plurality of indicia, such that at least one of the indicia is used to indicate a first position of the bite block relative to the backing plate, the first position being associated with a predetermined first dental imaging procedure; and a baseplate joining the post to the bite block, the baseplate extending along the first side of the baseplate so that in the first position, the bite block is positioned outward of the perimeter edge of the backing plate.

In another aspect, the present invention is directed to a dental x-ray image media holder comprising: a backing plate affixed to a bite block, the backing plate including a first side; a second side; a perimeter edge extending between the first side and the second side along the perimeter of the backing plate; a plurality of channels extending at least partially through the first side of the backing plate for receiving a post affixed to the bite block, such that the bite block can be selectively moved within the channels to orient the bite block in a predetermined position relative to the backing plate; and a plurality of indicia, such that a first indicia is used to indicate a first position of the bite block relative to the backing plate, the first position being associated with a predetermined first dental imaging procedure, and a second indicia is used to indicate a second position of the bite block relative to the backing plate, the second position being associated with a predetermined second dental imaging procedure; and a first locking member; and a baseplate joining the post to the bite block, the baseplate having a corresponding second locking member for engaging the first locking member of the backing plate so that upon engagement, rotational movement of the bite block about a post axis is prevented.

In another aspect of the present invention, it is contemplated that the dental x-ray image media holder has one or any combination of the following features: a baseplate joining the post to the bite block, the baseplate extending along a first side of the baseplate so that in the first position, the bite block is positioned outward of a perimeter edge of the backing plate; the baseplate includes a proximal end portion affixed to the post and a distal end affixed to the bite block, the bite block having a contact surface extending generally perpendicularly to the first side of the backing plate; a plurality of straps are secured to a second side of the backing plate such that after an image media is placed into physical contact with the second side of the backing plate, the straps can be wrapped to physically impinge upon the image media thereby securing it in position relative to the backing plate, and wherein the straps include perforations for removing the backing plate after securement to the image media; the post has base such that when positioned within at least one of the channels, a portion of the backing plate is received between the base and the baseplate with the post extending between and connecting the base and the baseplate; the backing plate is provided with at least two intersecting the channels, the channels include a t-shaped configuration made up of a primary channel intersecting a secondary channel at a midpoint of each the primary and secondary channels; the baseplate includes a proximal end portion affixed to the post and a distal end affixed to the bite block, the bite block having a contact surface extending generally perpendicularly to the first side of the backing plate; a locking member configured to prevent rotational movement of the bite block along a post axis upon engagement of the locking member; the locking member includes a first locking member having at least one groove and a corresponding second locking member having at least one rib, such that upon engagement of the rib within the groove, rotational movement of the bite block along the post axis is prevented; the backing plate includes a first locking member and the baseplate includes a corresponding second locking member such that upon engagement of the first locking member and the corresponding second locking member, rotational movement of the bite block about the post axis is prevented while permitting generally parallel movement of the bite block within the channel relative to the first side of the blacking plate; the backing plate is provided with at least two intersecting the channels, the channels include a t-shaped configuration made up of a primary channel intersecting a secondary channel at a midpoint of each the primary and secondary channels; a plurality of straps are secured to a second side of the backing plate such that after an image media is placed into physical contact with the second side of the backing plate, the strap can be wrapped to physically impinge upon the image media thereby securing it in position relative to the backing plate; the first locking member includes at least one longitudinally extending groove and at least one transversely extending groove along the first side of the backing plate and the corresponding second locking member includes at least one rib such that upon engagement of the first locking member and the corresponding locking member, the at least one rib is received within at least one of the at least one longitudinally extending groove and the at least one transversely extending groove; the baseplate extends along the first side of the baseplate so that in the first position, the bite block is positioned outward of the perimeter edge of the backing plate; the post has base such that when positioned within at least one of the channels, a portion of the backing plate is received between the base and the baseplate with the post extending between and connecting the base and the baseplate; or any combination thereof.

DETAILED DESCRIPTION

Figure 1:
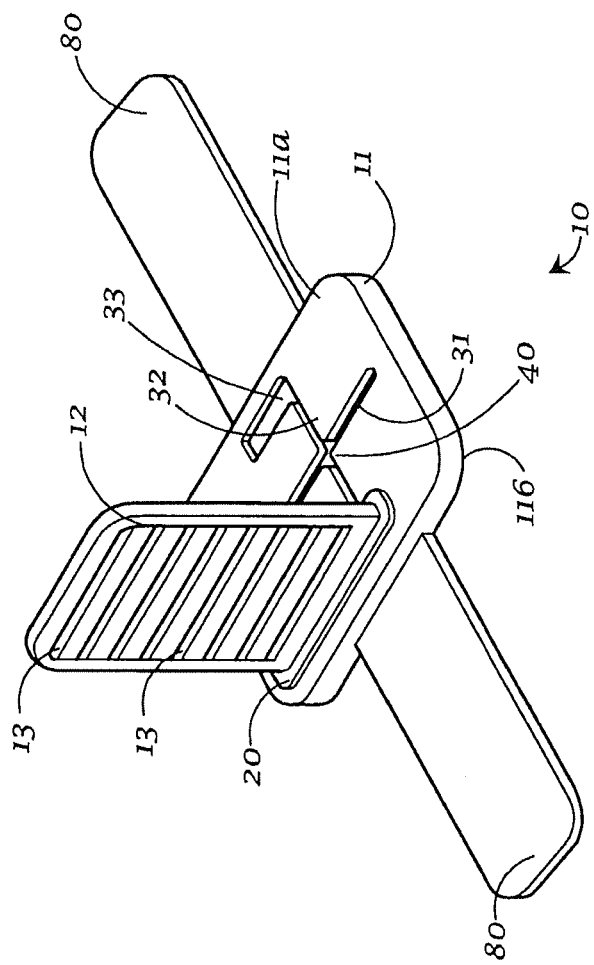
FIG. 1 is a perspective view of a dental image media holder embodying the concepts of the present invention.

An image media holder embodying the concepts of the present invention is generally designated on the attached drawings by the number 10. Image media holder 10 has a backing plate 11 configured to have a first side 11a, a second side 11b and a perimeter edge 11c. In one embodiment, the perimeter edge 11c extends between the first side and the second side along the perimeter of the backing plate. While backing plate 11 may be of any size or shape, it has been found that a generally rectangular and flat plate is conducive to physically contacting and supporting a dental x-ray image media in a manner to be hereinafter described. Of course, any size, shape or configuration is within the scope of the invention although it will be exemplified and is preferred to be of the flat plate design as shown on the drawings.

Image media holder 11 is also provided with a bite block 12. It will be understood by those skilled in the art that a "bite block" used with a dental x-ray image media holder is intended to be physically impinged between the teeth, gums or other patient dentition during x-ray procedures. As is convention, the image media holder will be positioned in a patient's oral cavity (not shown) and the patient will be instructed to bite upon the block. This locates the affixed or supported x-ray image media during the ensuing dental imaging procedure. Bite block 12 of the invention is of any suitable and conventional design, shape or configuration except for the unique inventive aspects to be described hereinbelow.

In one embodiment, bite block 12 may be generally flat and rectangular, and may be provided with at least one contact surface (e.g., two opposing contact surfaces) having optional gripping ridges 13 as is typically conventional. The bite block 12 may be provided with a baseplate 20 at one end thereof, preferably at one of the ends 12a (e.g., shorter ends) of its rectangular body if a rectangular design is chosen. Baseplate 20 is configured to be generally smooth such that intimate physical contact between it and first side 11a of backing plate 11 can be made. Preferably, that physical contact may be such that baseplate 20 can slide across the surface of first side 11a of backing plate 11 for purposes that will become clear from the following discussion. It is appreciated that the baseplate 20 may be a separate component attached to the bite block 12 or integrally formed therewith.

Figure 12:
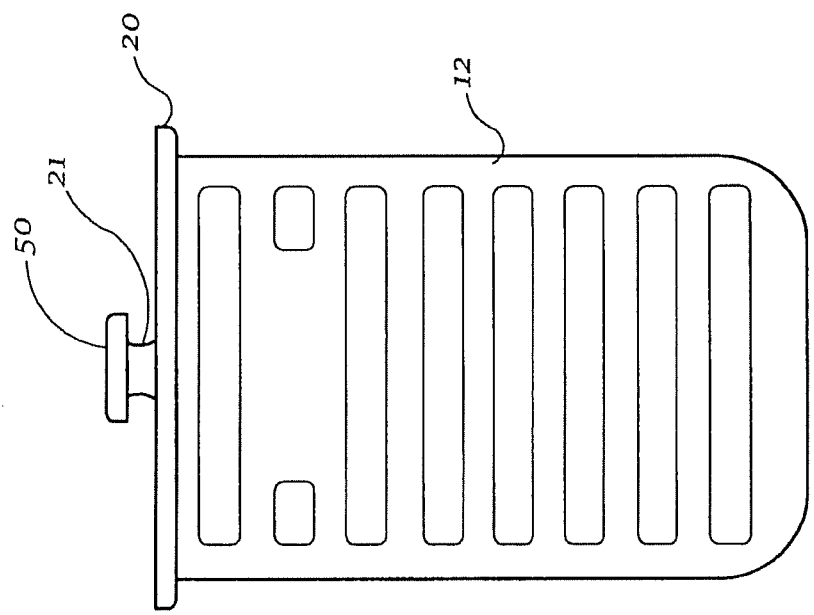
FIG. 12 is a front elevational view of the bite block component of the holder of FIG. 1.

Extending from bite block 12, and more preferably from baseplate 20, may be a positioning post 21 (FIG. 12) that will cooperatively interact with backing plate 11 in a manner to now be described. The positioning post extending along an axis PA. It is appreciated that the positioning post 21 may be integrally formed with or attached to the bite block 12, the baseplate 20, or a combination of both.

In a preferred embodiment, bite block 12 may be provided with a baseplate 20a at one end thereof (FIGS. 18-27). Baseplate 20a may be generally flat and rectangular (or otherwise shaped), and may include a proximal end 22, a distal end 23, a first side 24, and a second side 25. Typically, the baseplate 20a may extend generally transversely (e.g., perpendicularly) to bite block 12, though not required (e.g., such as extends diagonally or otherwise therefrom). For example, in one embodiment, the bite block 12 extends generally perpendicularly from the baseplate 20a (e.g., the first side 24) at the distal end 24 thereof. It is appreciated that the baseplate 20a (e.g., second side 25) may be positioned along the backing plate 15 (e.g., first side 11a) in an adjacent manner such that the distal end 23 extends beyond the perimeter edge 11c of the backing plate. As such, the extended base plate 20a provides for an offset of the bite block 12, which is located at the distal end 23 thereof so that the bite block 12 (e.g., the entire bite block 12) may also be positioned outward of the perimeter edge 11c of the packing plate.

Figure 24:
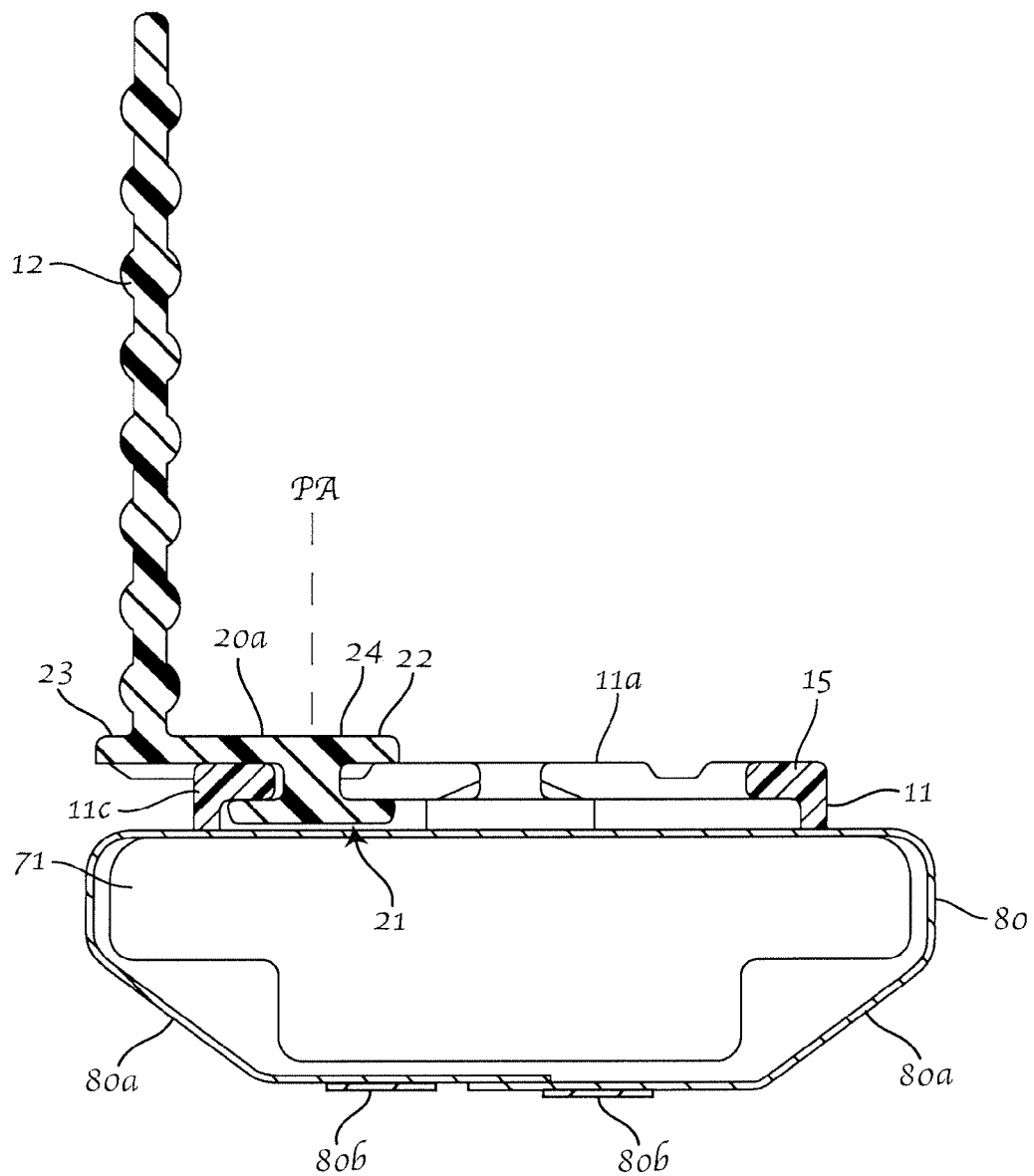
FIG. 24 is a cross-sectional side view of the alternative embodiment shown in FIG. 18, shown with an exemplary dental x-ray sensor for environmental purposes.

In this arrangement, the positioning post 21 may be located at the proximal end 22 of the baseplate 20a (e.g., extending from the bottom surface 24) so that the bite block 12 may be positioned in a spaced apart (e.g., offset) arrangement relative to a post axis PA of the positioning post 21 (FIG. 24). For example, as shown in FIG. 24, the distal end 23 is extended outward from (e.g., beyond) the perimeter edge 11c of bite block 12 so that the bite block 12 may be positioned outward (e.g., offset) from the backing plate 11. The offset of bite block 12 allows for the image media holder 10 to accommodate different size sensors (e.g., size 1 sensor, size 2 sensor, or otherwise sized sensors) so that the backing plate may be generally centered about the active area of the sensor, which may be desirable for increased positioning range.

Figure 3:
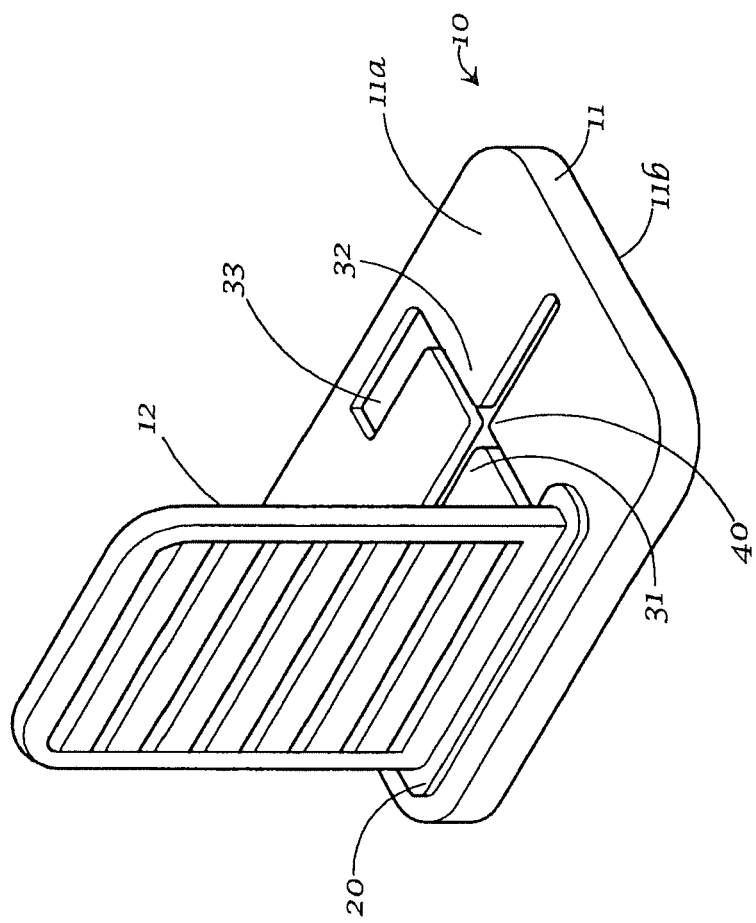
FIG. 3 shows the image media holder of FIG. 2 with the bite block in still another position.

In order to allow bite block 12 to be positioned in more than one position relative to the backing plate, there is preferably provided in backing plate at least one and preferably a plurality of slots or channels. For example, in one embodiment with reference to FIG. 3, the backing plate 11 may be provided with channels 31-33. In another embodiment, for example with reference to FIG. 17, the backing plate may be provided with channels 31a and 32a. In yet another embodiment, for example in another embodiment, with reference to FIG. 18, the backing plate 15 may be provided with channels 31b and 32b. The channels may be of any design or configuration and may extend completely through backing plate from first side 11a to second side 11b. Alternatively, the channels may extend only partially through from first side 11a and not all the way to second side 11b.

Figure 2:
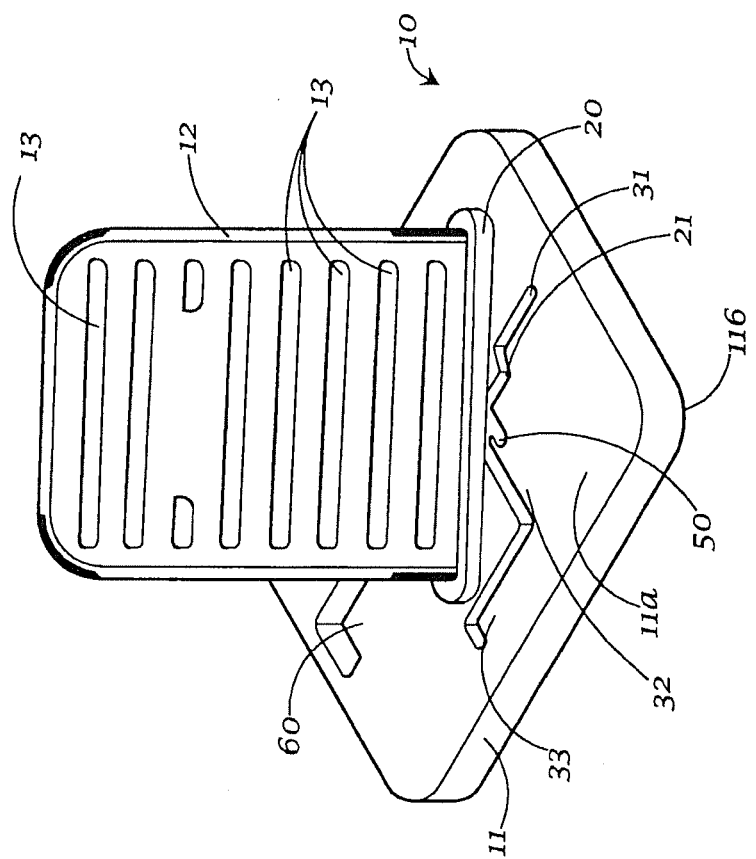
FIG. 2 is a perspective view of a portion of the image media holder of FIG. 1, showing a bite block in a position where adjustment thereof relative to a backing plate can take place.

Post 21 affixed to the bite block and/or the baseplate may be configured such that it can be received within channels. By sliding within a selected one of channels to any preselected position therein, it will be appreciated that bite block can be so positioned wherever it is desired. Furthermore, the post 21 may be provided in any shape (e.g., square, rectangular, circular or otherwise) and/or size. As such, the media image holder 10 may further include a locking means for limiting and/or substantially preventing rotation of the baseplate relative to the backing plate upon engagement thereof. In one embodiment, post 21 may be provided in a generally square-shape so that rotation of the bite block 12 may be limited or substantially prevented along one or more portions of the respective channel (such as a locking means comprising one or more channel walls or otherwise that prevent rotation of the square post), though not required. It is appreciated that when rotation is limited or substantially prevented along a channel, the channels may be configured to allow rotation of the bite block 12 at an intersection therebetween (FIGS. 2 and 18) having an expanded area 60 as discussed herein.

In a preferred embodiment, post 21 may be provided in a generally circular-shape to allow rotation of the baseplate along one or more portions of the channel. The locking means may include one or more locking members that upon engagement of the one or more locking members, movement of the bite block 12 is limited or substantially prevented in at least one direction within the respective channel or channels. Preferably, upon engagement of the locking member rotational movement of the bite block 12 about the post axis PA may be prevented. More particularly, it is appreciated that upon engagement of the locking members, rotation of the bite block may be prevented while the bite block may be free to selectively move within the channels in one or more other directions relative to the backing plate (e.g., forward and backwards, left and right, or otherwise). In one embodiment, the locking member includes a first locking member and a corresponding second locking member each configured to engage the other to limit or substantially prevent movement of the bite block in at least one direction within a channel. It is appreciated that the locking members (e.g., the first locking member, the corresponding second locking member, and/or otherwise may be of any size, shape or configuration is within the scope of the invention although it will be exemplified and are preferred to have interlocking features (e.g., mating) so that movement by one locking member relative to the other locking member in at least one direction may be limited or substantially prevented.

Figure 20:
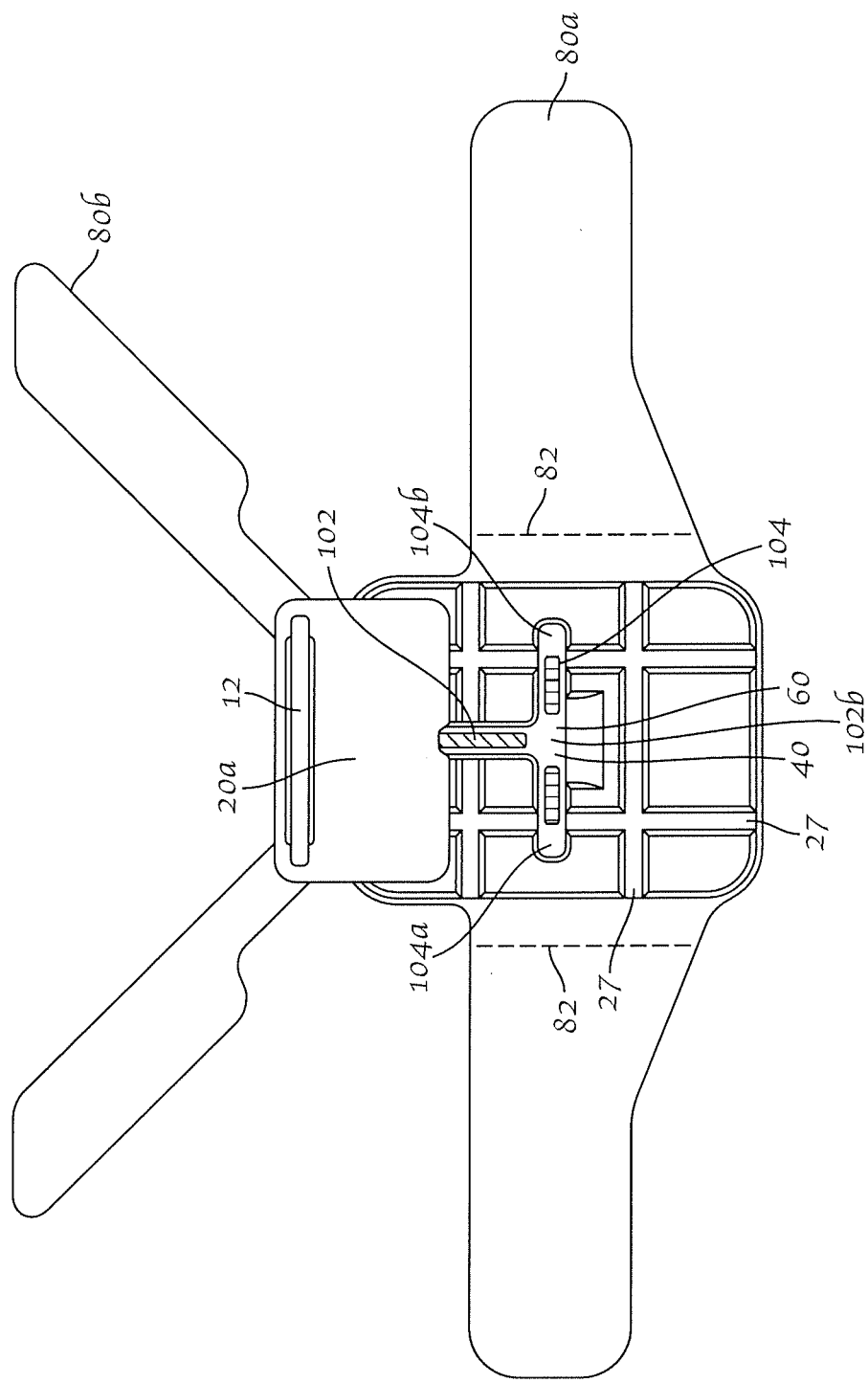
FIG. 20 is a top view of embodiment shown in FIG. 19.
Figure 21:
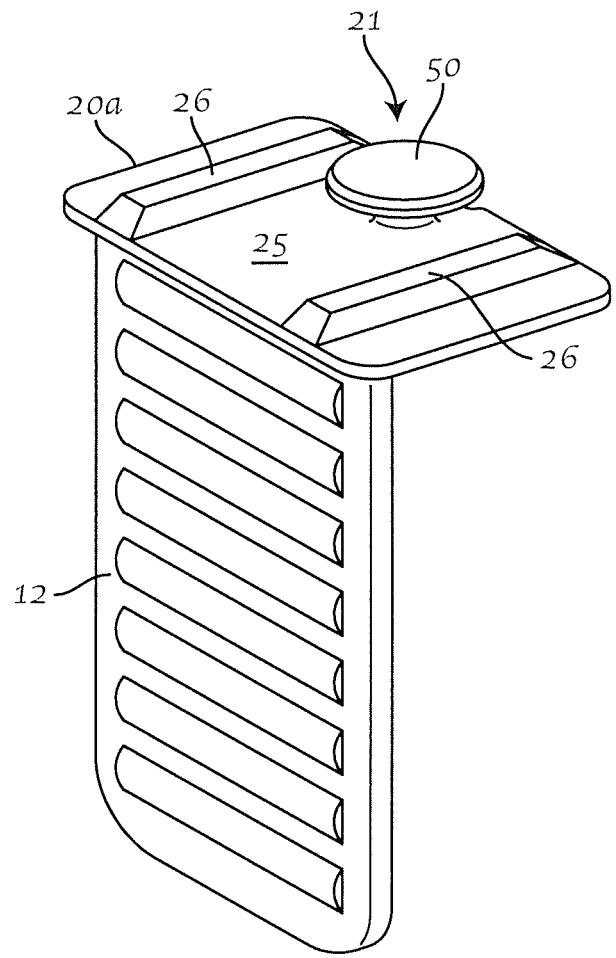
FIG. 21 is a perspective view of the bite block component shown in FIG. 18.
Figure 25:
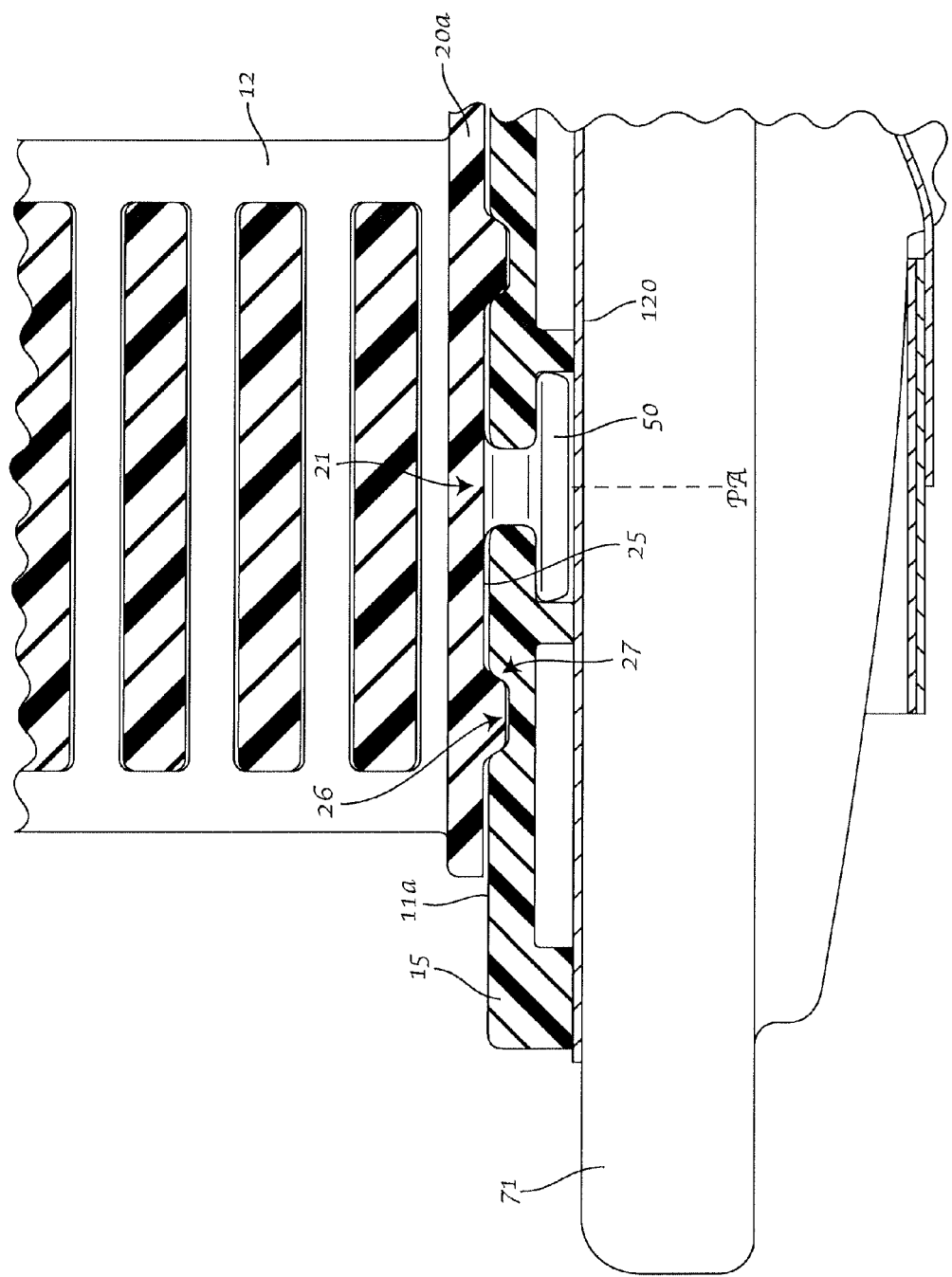
FIG. 25 is a close-up cross-sectional side view of a portion the alternative embodiment shown in FIG. 24, shown with an exemplary dental x-ray sensor for environmental purposes.

Typically, the backing plate may be provided with either the first locking member or the corresponding second locking member and the bite block (e.g., baseplate) may be provided with the other, though not required. For example the locking member includes a first locking member having one or more grooves 27 (e.g., provided along the first side 11a) and a corresponding second locking member having one or more ribs 26 (e.g., provided along the second side 25 of the baseplate 20a), to engage one another (e.g., mate, interact, intersect, or otherwise) so that rotation of the bite block 12 about the post axis PA may be limited or substantially prevented (FIG. 25). In one specific example, the backing plate includes the first locking member having a pair of longitudinal grooves and a pair of transverse grooves formed in the first side 11a of the backing plate. Each pair of grooves 27 include two generally parallel grooves having a spacing therebetween similar to the other pair of grooves. In doing so, as shown in FIG. 20 the longitudinal grooves intersect the transverse grooves thereby forming four intersections thereabout. Furthermore, the baseplate 20a includes a pair of ribs 26 generally formed along the second side 25 of the baseplate 20a, each rib being generally parallel to the other and having a similar spacing to that of each pair of the grooves 27. In this arrangement, upon engagement such that the ribs 26 are received within the grooves 27, rotation of the bite block about the post axis is substantially prevented while movement forward and backwards (e.g., bite block 12 being generally positioned within the pair of longitudinal grooves) or right to left (e.g., bite block 12 being generally positioned within the pair of transverse grooves) relative to the backing plate 15 may be permitted.

Figure 22:
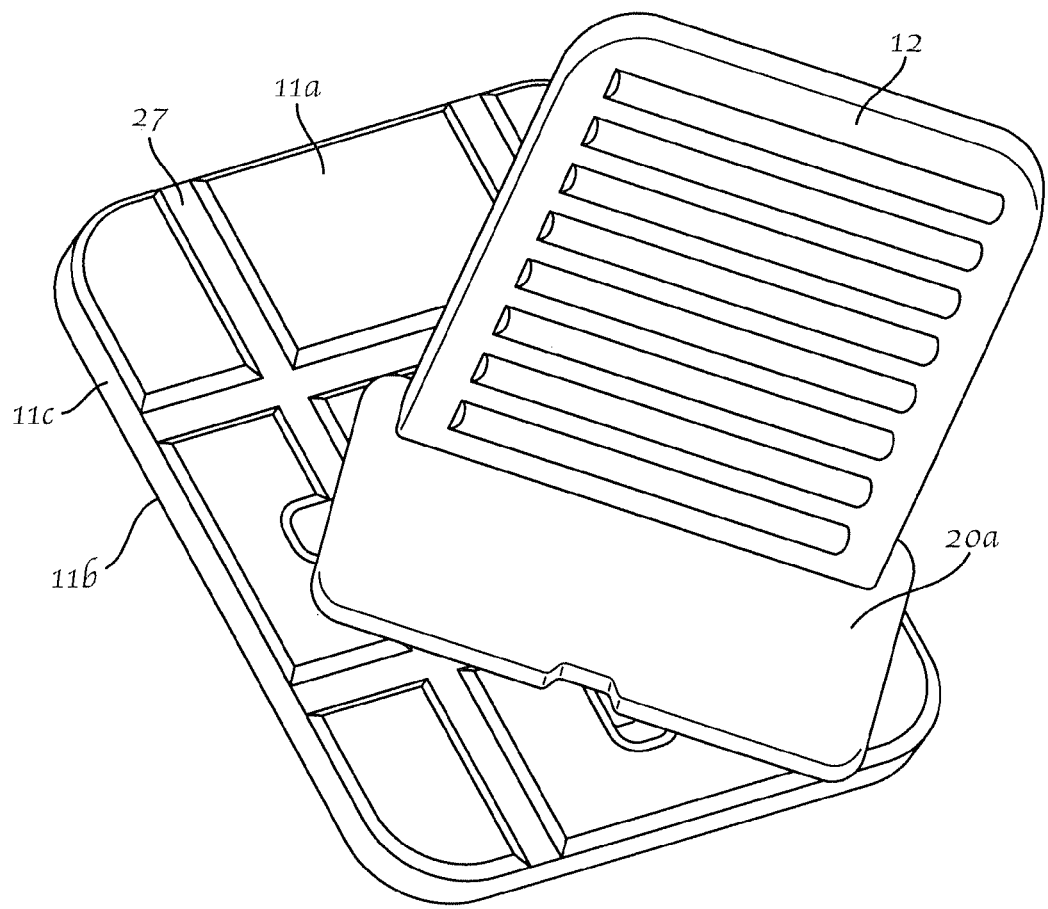
FIG. 22 is a perspective view of the alternative embodiment shown in FIG. 18 with the bite block component shown in an alternate position.
Figure 23:
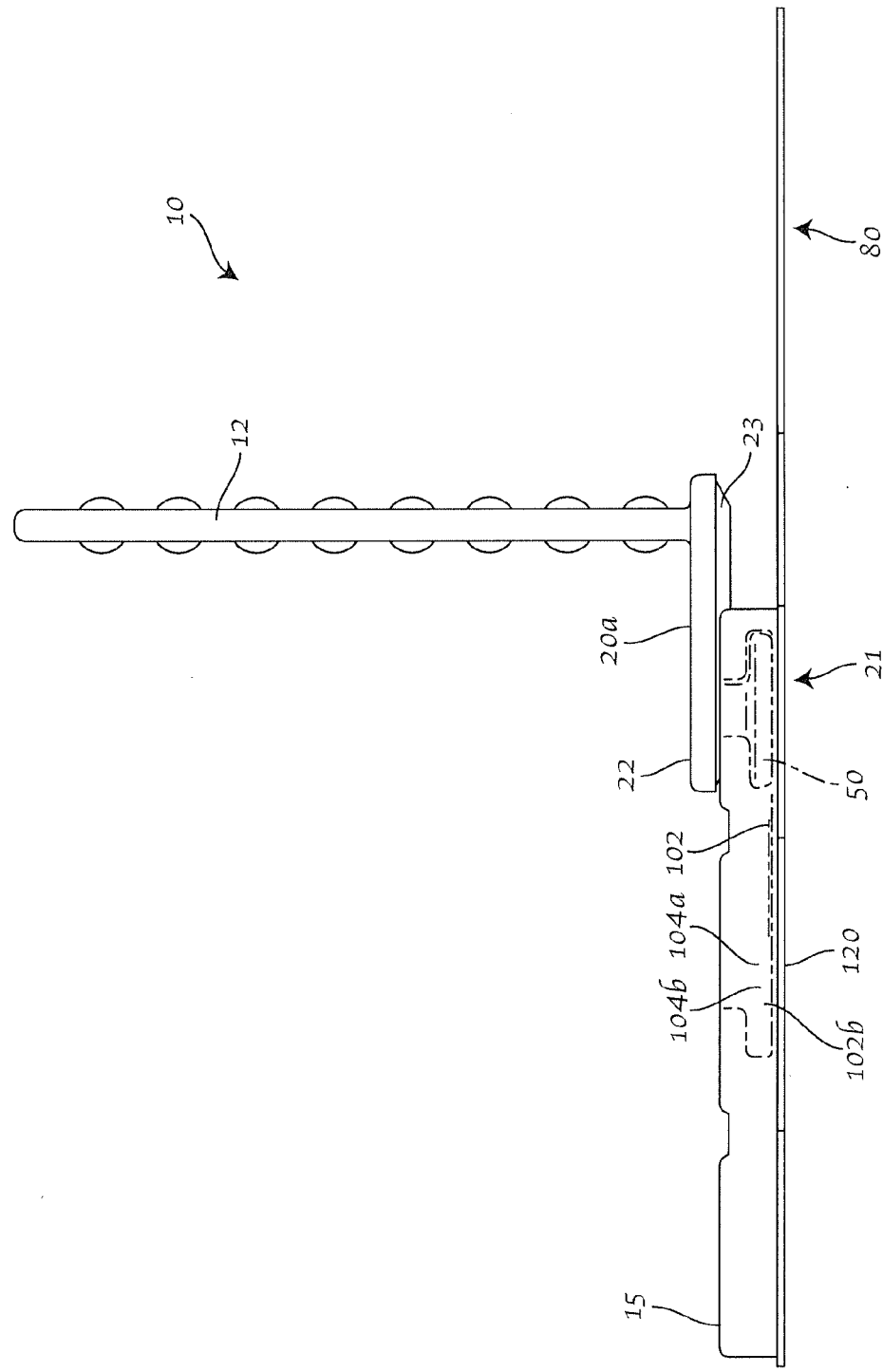
FIG. 23 is side view of the alternative embodiment shown in FIG. 19.

However, it is appreciated that, upon removing the ribs from the corresponding arrangement within the grooves 27 as shown in FIG. 22 (e.g., in an offset, generally non parallel, or otherwise arrangement), the bite block may generally, freely rotate relative to the backing plate. Removal of the ribs 22 from grooves 27 may be aided by additional force applied to the bite block in a twisting motion (e.g., rotating about the post PA) and/or by providing sloped edges in one or both of the ribs 26 or grooves 27, and/or otherwise. Once the ribs 22 are repositioned within the grooves (e.g., generally parallel thereto) the locking member is engaged and rotation about the post axis PA is again prevented. It is contemplated that the locking means may be provided as one integral component or several components and/or the locking means may be provided in various locations along one or more of the baseplate, backing plate, or otherwise. To allow positioning of the baseplate (e.g., bite block 12) relative to the backing plate and to accommodate at least the taking of dental x-rays to include anterior vertical periapical, anterior horizontal periapical, posterior horizontal periapical, posterior vertical periapical, horizontal bite-wing, vertical bite-wing or others, it is preferred to have at least a primary channel 31b and a secondary channel 32b, although of course, any number of channels of any design, shape or intersection is within the scope of the invention.

In one embodiment of the invention, channels 31-33 are substantially linear although any shape is within the scope of the invention. In this embodiment, primary channel 31 may intersect secondary channel 32 at some midpoint of the respective channels. By midpoint it is simply meant at some point between their respective ends. In a preferred configuration, the intersection 40 of primary channel 31 and secondary channel 32 is at the approximate center of secondary channel 32 and somewhat removed from the center of primary channel 31 such that the two from a "t". Tertiary channels 33 may intersect any other channels, but for the sake of the drawings a preferred embodiment is shown where each tertiary channel 33 at one of its own ends intersects an end of secondary channel 32.

In another embodiment of the invention, channels 31b-32b (FIG. 18) are also substantially linear although any shape is within the scope of the invention. In this embodiment, primary channel 31b may intersect secondary channel 32b at some midpoint of the respective channels. By midpoint it is simply meant at some point between their respective ends. In a preferred configuration, the intersection 40 of primary channel 31b and secondary channel 32b is at the approximate center of secondary channel 32b such that the two from a "T".

As stated above, the exact design, dimensions or other characteristics of the channels can be varied but they should be such that they can receive and guide post 21 and hence, bite block 12 (being attached to the baseplate). It will be appreciated that by sliding bite block 12 over the surface of backing plate, such sliding being guided by the physical contact of post 21 within a selected channel, bite block 12 can be positioned relative to backing plate in any desired location. It will be further appreciated that bite block can be moved from one channel such as primary channel to another channel such as secondary channel by moving post 21 (and hence the attached bite block 12) within the channel to the intersection thereof such as intersection 40 and thereby continue to move the post 21 to the other channel. Post 21 thus moves within a channel 31-33, 31a and 32a, or 31b and 32b in a sliding manner.

It is also preferred to provide a base 50 at an end of post 21 and provide channels that completely pass through backing plate 11 between its two sides 11a and 11b, such that the channels are open slots. Post 21 thereby extends between and connects the bite block or the baseplate if employed, and base 50. By configuring base 50 to be wider than the channels, and by configuring post 21 to be of suitable dimension, the backing plate can be caused to be physically received between base 50 and bite block 12. This physically affixes the bite block to the backing plate in an otherwise adjustable manner by use of the channels as already described. Again it will be appreciated that bite block 12 while being held to backing plate may be free to be positioned anywhere within the channels and may even be rotated on an axis or rotation provided by post 21, thereby accommodating any or all of the numerous x-ray positions required by a dental practitioner.

In a preferred embodiment, the bite block 12 is rotated on post 21 with post 21 acting as an axle or rather its axis acts as an axis of rotation. In a further embodiment, post 21 and channels 31-33 are configured and dimensioned in shape or size such that bite block 12 can be rotated only at an intersection of at least two channels 31-33, although this is not necessarily required. In yet a further embodiment, post 21 and the channels 31b and 32b may be configured and dimensioned in shape or size such that bite block 12 can be rotated along any portion of two channels 31b and 32b, however, rotation may be limited or substantially prevented while the locking means is engaged. For example, as discussed above, the locking means may be engaged when the first locking member and the corresponding second locking member interconnect (e.g., the grooves and ribs are in general alignment). Thereafter, the locking means may be disengaged to allow rotation by removing the first locking member from the corresponding second locking member (e.g., the grooves and ribs are not in general alignment). This may be accomplished by applying sufficient pressure to at least one of the bite block or baseplate while generally maintaining the other in place.

A larger opening or expanded area 60 may be provided in one or more channels, of such size as to pass base 50 to aid assembly of the image media holder 10 component parts. Expanded area may also provide an area where post 21 can be more easily rotated therein. In one embodiment, the expanded area may include one or more passing portions 62 (e.g., angled, sloped, flanged or otherwise portions) to aid in passing the base 50 through the expanded area 60 for assembling (e.g., fixedly or removably securing) the bite block to the baseplate. Optionally, the passing portions 62 (and/or one or more separate withdrawal portions, not shown) may also aid in limiting or substantially preventing withdrawal of the bite block from the baseplate, once assembled.

In a preferred embodiment of the invention, image media holder 10 is fabricated from any suitable material usable in the oral cavity. More preferred image media holder 10 is fabricated from a plastic material and the image media holder 10 is disposable.

There is also provided according to the invention some means of securing or affixing, preferably in a removable manner, an image media such as imaging plate 70 and digital sensor 71 to the second side 11b of the backing plate. Two preferred methods include a releasable or pressure-sensitive adhesive (not shown) and one or more straps 80, which may be used separately or in combination with each other.

Figure 4:
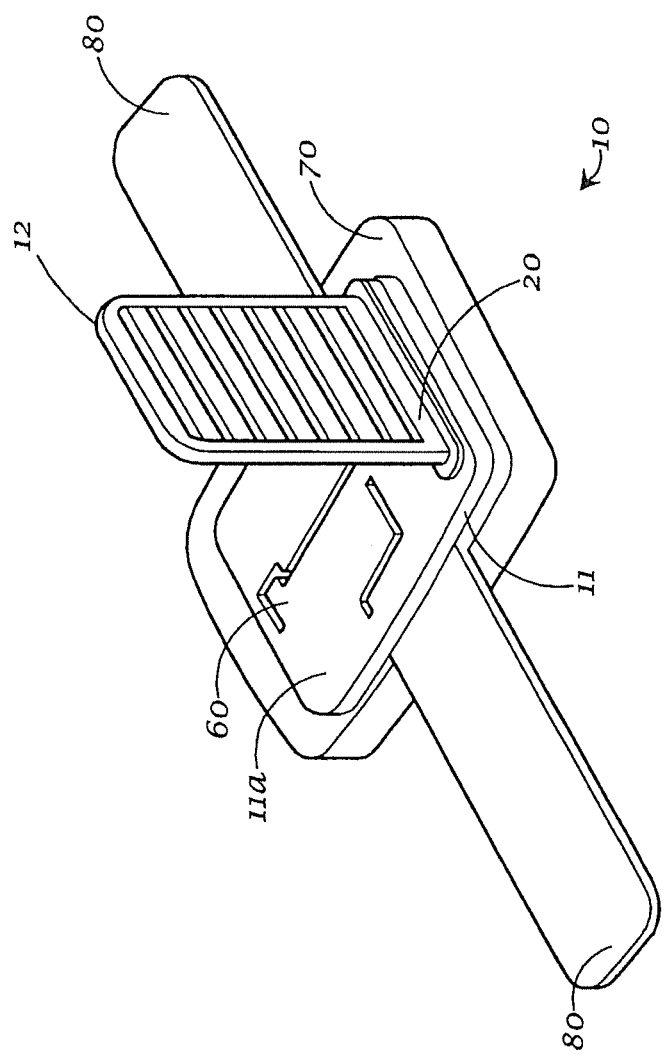
FIG. 4 is a perspective view of the image media holder as in FIG. 1, showing a bite block adjusted to a different position.

Any adhesive suitable for use in the oral cavity is within the scope of the invention, and the specific adhesive chosen is not necessarily a limitation of the invention. One preferred adhesive is a latex-free, pressure-sensitive adhesive which is coated onto second side 11b of the backing plate in any conventional manner. A release strip (not shown) may be employed to cover the adhesive until used. As shown for example, in FIG. 4 and FIG. 24, an image media such as plate 70 or sensor 71 can be physically pressed onto second side 11b of the backing plate and held in place by the pressure-sensitive or other adhesive employed.

Figure 26:
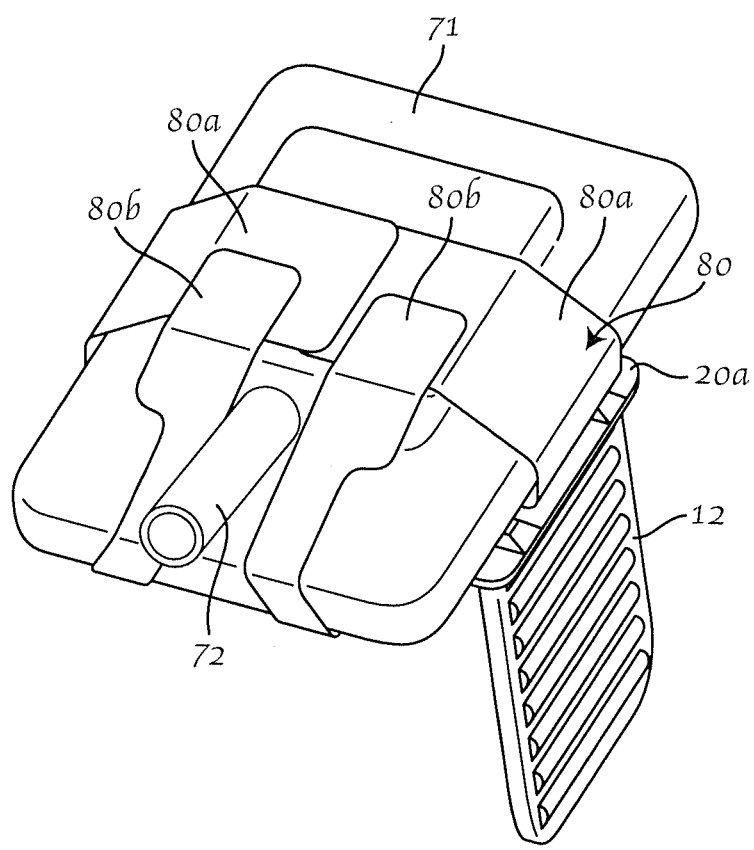
FIG. 26 is a bottom perspective view of the alternative embodiment shown in FIG. 24 shown with an exemplary dental x-ray sensor for environmental purposes.
Figure 27:
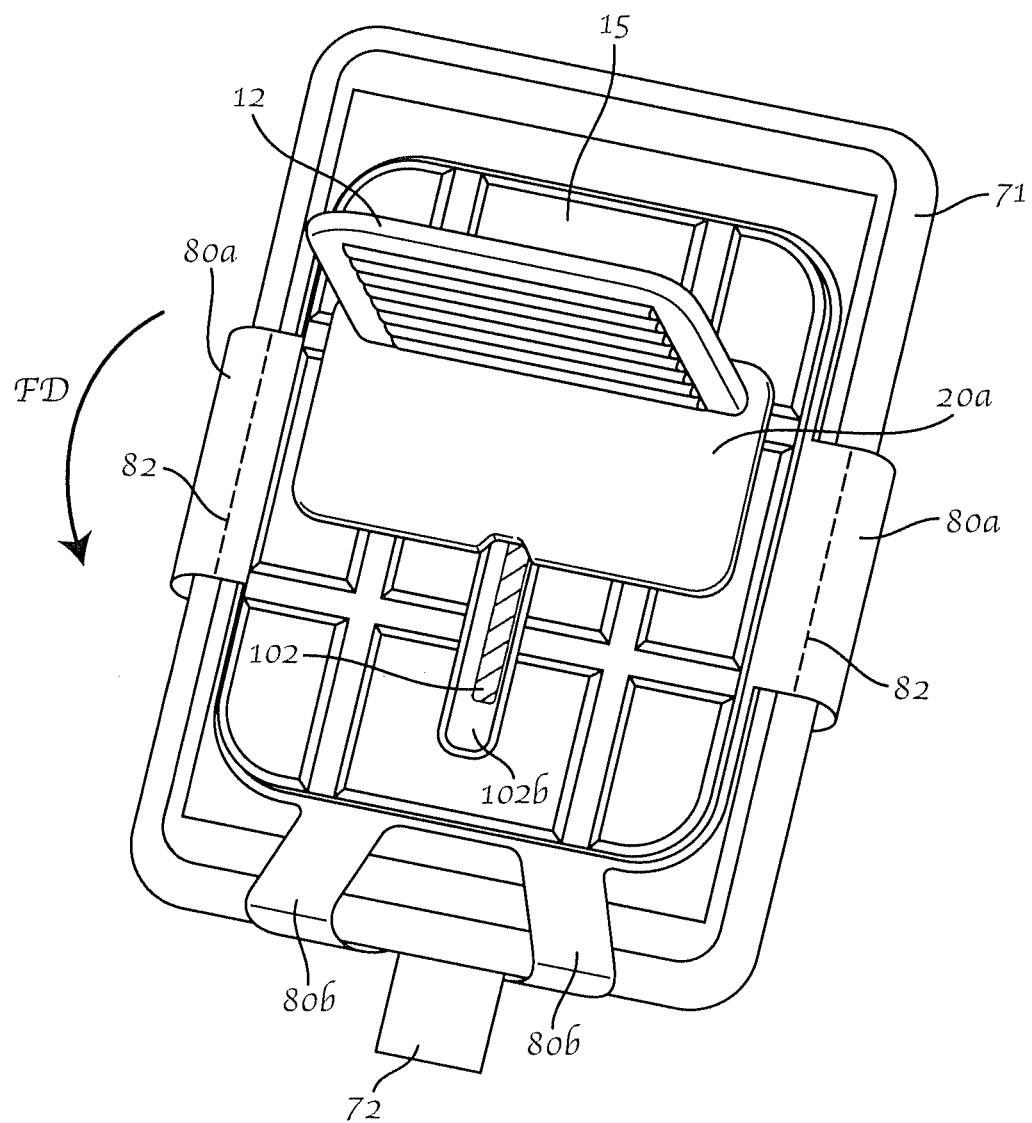
FIG. 27 is a top perspective view of the alternative embodiment shown in FIG. 24 shown with an exemplary dental x-ray sensor for environmental purposes.

If a strap 80 is employed and at least two are preferred, it may be affixed to the backing plate and is preferably flexible in one direction yet rigid in another. Once the image media such as plate 70 or sensor 71 is caused to physically contact the backing plate, strap 80 (or straps 80 if more than one are used) may be partially or completely wrapped around plate 70 (or any other imaging media as may be employed) in a manner allowed by the flexibility of strap 80, to thereby hold the imaging media to the backing plate 11, 15 (FIGS. 7, 8, 24, 25, and 27). For example, FIGS. 24, 26, and 27 provide a first pair of straps 80a that generally (e.g., completely) wrap around the sensor 71 (e.g., transversely about the sensor from two different sides of the backing plate as shown) and a second pair of straps 80b that at least partially wrap around sensor 71 (e.g., longitudinally about the sensor from the same side of the backing plate as shown). When included, the second pair of straps 80b, may provide additional securement of the holder 10 to the sensor 71 (e.g., to limit or substantial prevent longitudinal movement of the sensor). The straps 80b may also aid in limiting or substantially preventing movement of the connecting wire 72, though not required.

Straps 80 may also be provided with a suitable adhesive or they may be provided with any other conventional means to affix them in the securing position. By all such manner or combinations thereof, straps 80 and/or the adhesive positively secure and otherwise affix (preferably in a removable manner) an imaging media to holder 10.

Furthermore, one or more of the straps 80 may also be provided with at least one perforation 82 that can be ruptured (e.g., torn) to aid in the removal of the image media holder 10. In one particular embodiment, straps 80 include transverse perforations 82 that generally correspond to and extend along an edge portion of the sensor 71 (FIG. 27), though it is contemplated that perforations may be provide anywhere along the straps 80 and about the sensor 71 respectively. It is appreciated that by applying a force to the image media holder 10 (e.g., bite block) in a force direction FD generally opposing and/or away from the sensor 71 (e.g., generally along the direction of the perforations), the perforation 82 may be ruptured so that at least a portion of the media holder or the entire media holder may be removed from the sensor. It is appreciated that the perforations 82, aids in improving releasability of the image holder from the sensor.

Figure 5:
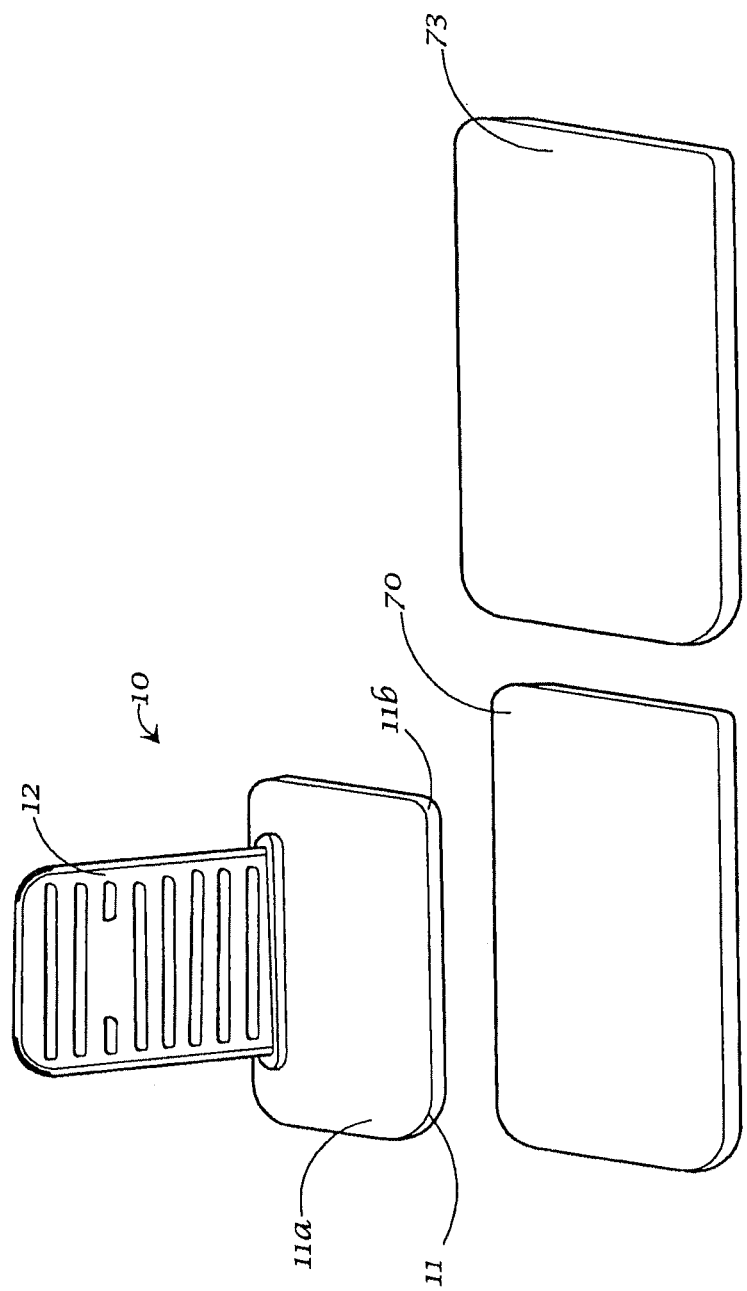
FIG. 5 is a partially exploded view of an image media holder as in FIG. 2 shown for environmental purposes in conjunction with a phosphor imaging plate and a barrier envelope for the phosphor plate.
Figure 6:
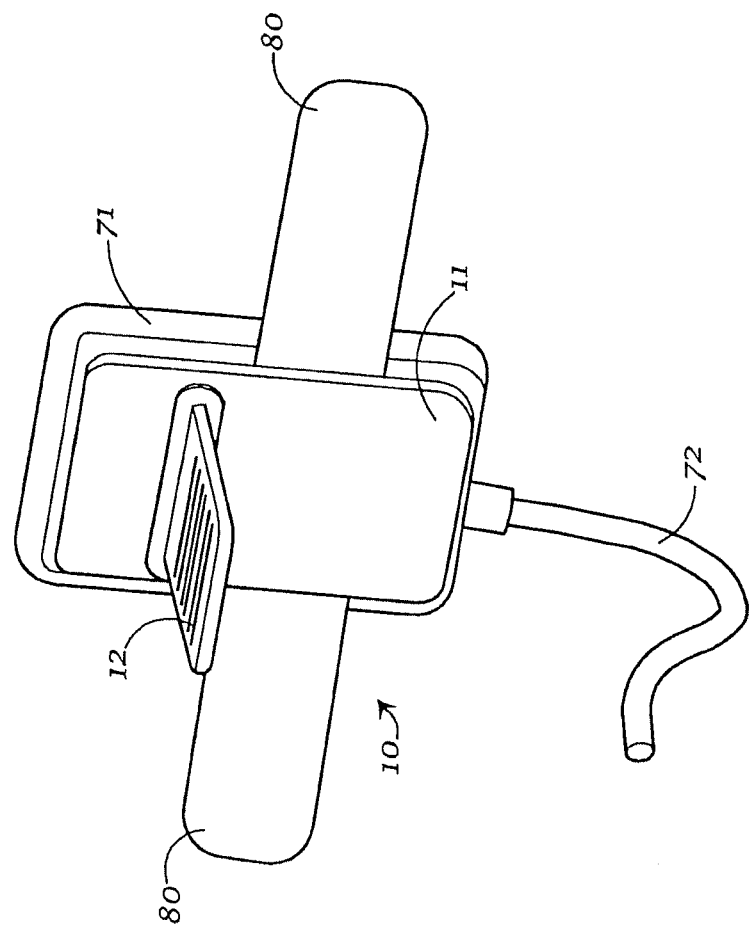
FIG. 6 is a top perspective view of an image media holder as in claim 1, shown for environmental purposes holding a digital dental sensor having an attached cord (partially shown).
Figure 7:
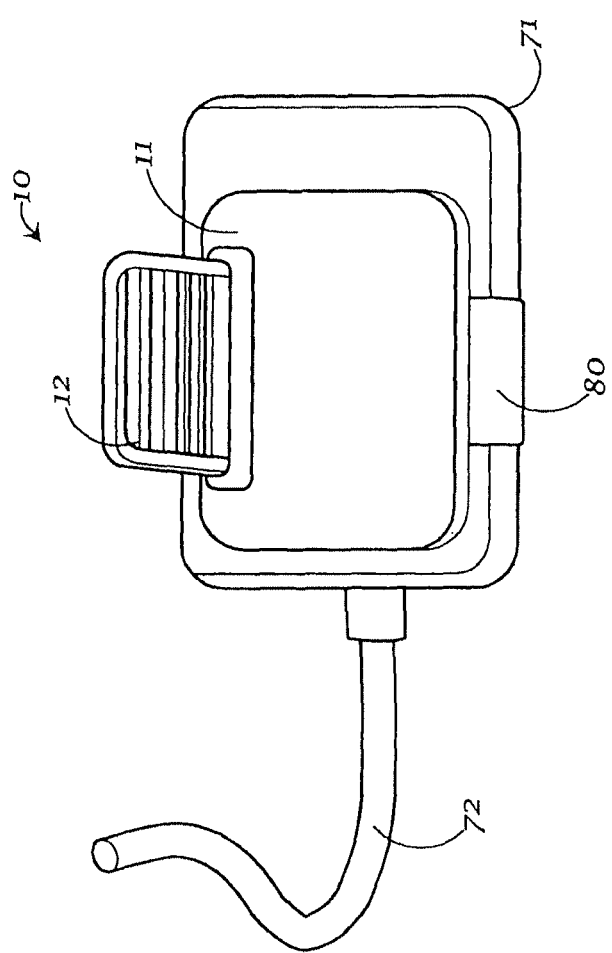
FIG. 7 is a top perspective view of the image media holder of FIG. 6, showing a means of affixing an image media to the image media holder.
Figure 8:
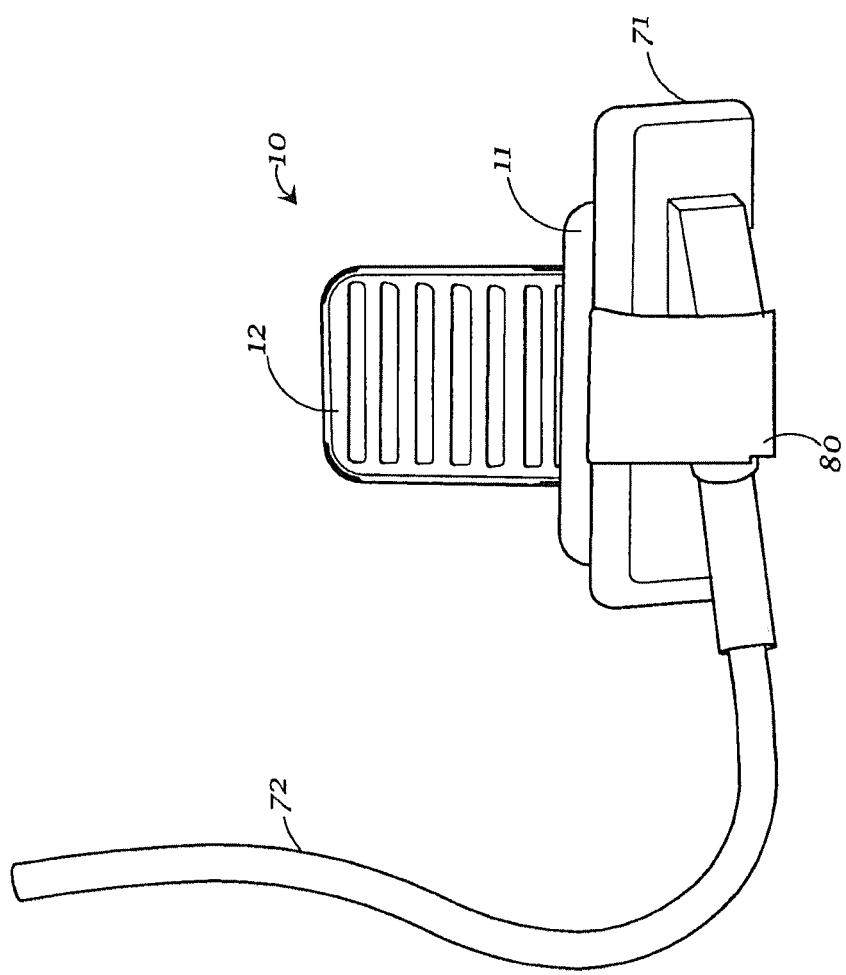
FIG. 8 is a bottom perspective view of the image media holder of FIG. 7.
Figure 9:
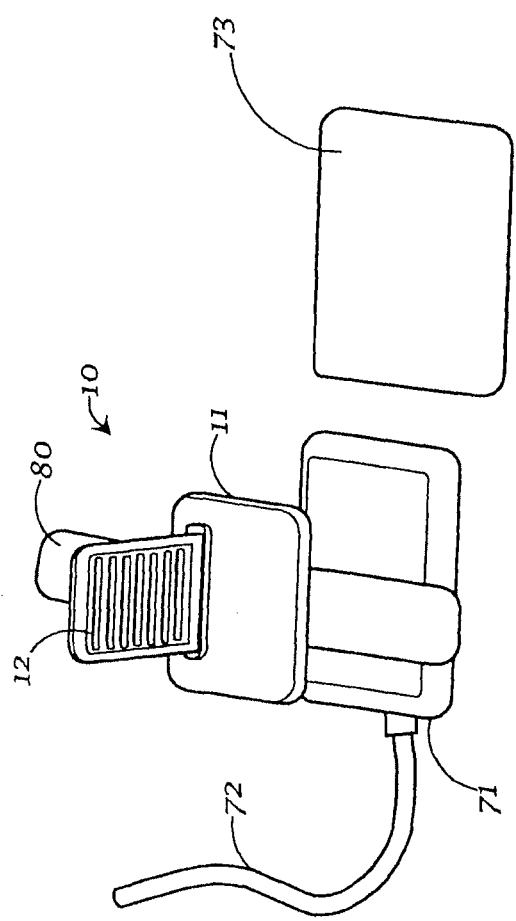
FIG. 9 is a partially exploded view of the image media holder of FIG. 6, showing for further environmental purposes a cover sleeve for the image media.

It will be appreciated that by suitably designing straps 80, any of a large number of image media designs such as for example, plate 70 or digital sensor 71 can be held by image media holder 10. Just as a belt may be adjusted to secure items of different size or shape, strap 80 may also accommodate different imaging media due to the length or other dimensions of strap 80. The design can accommodate different image media such as plate 70, relatively thicker image media such as digital sensor 71, and even other items such as connecting wire 72 for digital sensor 71 or conventional protective sleeves or barriers 73 (FIGS. 5 and 9) for such image media. Although not depicted, a conventional dental x-ray film packet or indeed any other dental image media can be held by the inventive image media holder 10. It is even contemplated that the present invention can secure and hold such imaging media as may be developed in the future.

Figure 10:
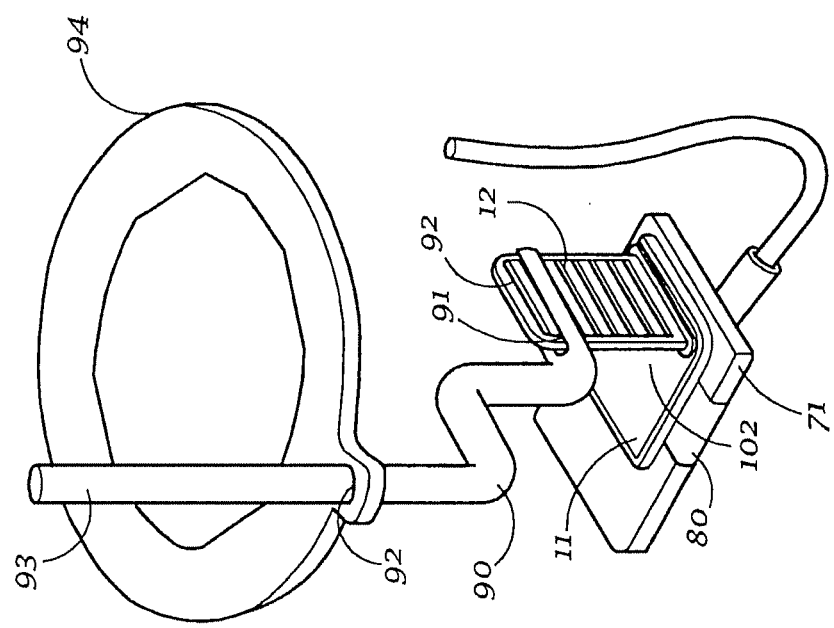
FIG. 10 is a perspective view of an alternative embodiment of an imaging media holder according to the present invention, and shown with an attached arm and aiming ring.
Figure 11:
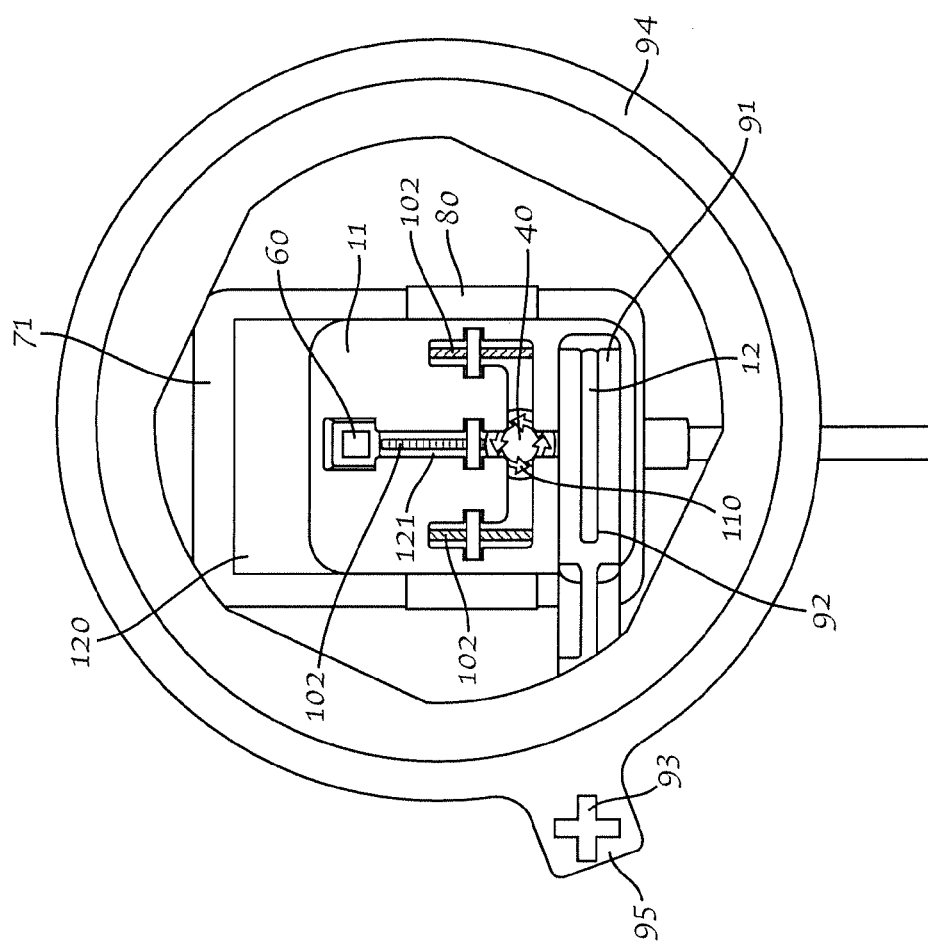
FIG. 11 is a top plan view of the holder of FIG. 10.

It is known in the dental x-ray art to provide aiming rings mounted upon arms or other structures to in turn, effectively connect the aiming ring to an imaging media holder. The present invention can be so configured as is shown in FIGS. 10 and 11. Any means of affixing an arm and aiming ring to holder 10 is within the scope of the invention. One preferred means is to provide an arm 90 having a fixing member 91 provided with a slot 92. Slot 92 may be configured and sized to physically receive and frictionally hold an edge of bite block 12 therein. At location distal to fixing member 91 is a support post 93 which is configured to receive or otherwise adjustably secure an aiming ring 94 thereto. For example, post 93 may have a certain shape such as the cross-shape depicted in the drawings and a complementary shaped aperture 95 may be provided at some location in aiming ring 94, such that post 93 is placed through aperture 95 in use. Aiming ring 94 is free to slide along post 93 to any desired position and is frictionally held in place by its physical contact with post 93.

In an alternative embodiment of the invention (FIGS. 10, 11, and 20), a backing plate may be provided with indicia 102 which separately indicate a different position for a specific x-ray procedure. Indicia 102 may be colors, numbers, letters, symbols, protrusions, detents, striations, or any other physical or visual indicators without limitation, or even combinations thereof. For example, the backing plate may be provided with more than one distinct indicia 102 (e.g., first indicia 102a, second indicia 102b, etc. . . . ), which might indicate for example, by different colors the position to which bite block 12 should be moved to take a left bitewing or a right bitewing respectively. Further still, if holder 10 is of the type wherein bite block 12 can be rotated on post 21 as an axis of rotation and only at a certain point such as the intersection of certain channels 31-33 or generally anywhere along channels 31b and 32b so long as the locking member is not engaged. In specific embodiments where rotation may be available at a certain point such as an intersection, further indicia such as indicia arrows 110 may be provided at the intersection or other area where such rotation is permitted.

Indicia 102 and 110 may be provided on a separate layer of material, such as a plastic sheet 120 which can be positioned in a juxtaposed physically contacting relationship with second side 11b of backing plate 11. In a preferred embodiment, straps 80 and integrally formed with and from the same material as sheet 120. In this configuration, it may be advantageous to provide a backing plate which is at least partially transparent, such that indicia 102 placed upon sheet 120 may be viewed therethrough. While it will be appreciated that a transparent or at least partially transparent backing plate will facilitate viewing the indicia 102 or 110 therethrough when sheet 120 is employed, it is also possible to simply provide large enough openings 121 in bite block 100 so as to view indicia 102 or 110 therethrough. Further still, channels 31-33, 31a and 32a, or 31b and 32b may themselves be suitably positioned such that the indicia 102 and/or 110 may be viewable therethrough.

In one embodiment, the backing plate may include indicia 102 having a plurality of indices (e.g., 102a, 102b, etc. . . . ), each corresponding to at least one position for one or more dental x-ray procedures (and optionally corresponding to indicia 102 and/or 92a' of the aiming ring). For example, a first indicia may be associated with a first position for taking a first x-ray procedure and optionally a second position for taking a second x-ray procedure. It is appreciated that various positions and/or orientations about indicia 102 may be obtained by way of rotating the bite block, moving the bite block along a channel, or both. In one particular embodiment as shown in FIG. 20, the backing plate 15 may include a first indicia 102 having a first position 102a that may be associated with performing a first dental x-ray procedure and a second position 102b that may be associated with performing a second dental x-ray procedure. The backing plate 15 may further include and a second indicia 104 having a first position 104a that may be associated with performing a third dental x-ray procedure and a second position 104b that may be associated with performing a fourth x-ray procedure. In this configuration, the first position 102a may be located at one position along the primary channel (e.g., generally positioned at an end portion of the primary channel) and the second position 103b may be located at another location along the primary channel (e.g., generally positioned at the intersection of the primary and secondary channels). Furthermore, the first position 104a may be located at one position along the secondary channel (e.g., generally positioned at an end portion of the secondary channel) and the second position 104b may be located at another location along the secondary channel (e.g., generally positioned at an opposite end portion of the secondary channel).

Figure 13:
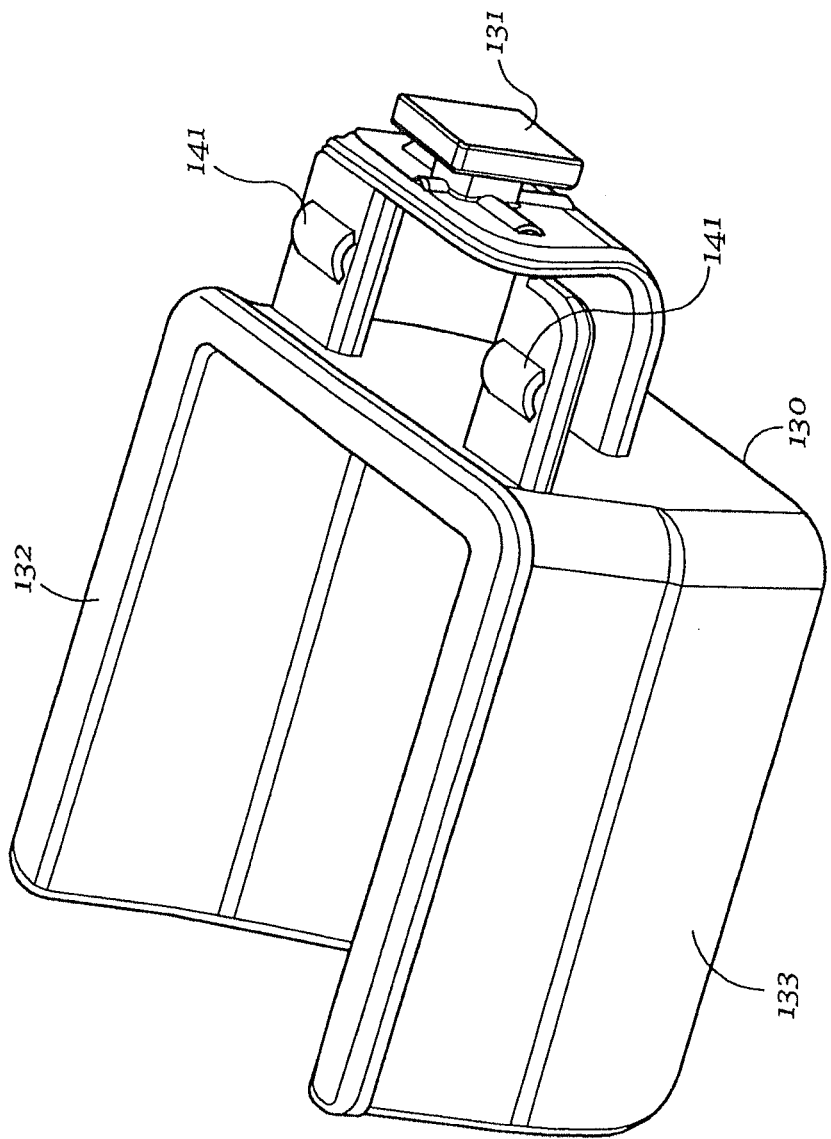
FIG. 13 is a perspective view of an alternative bite block useful with the present invention.
Figure 14:
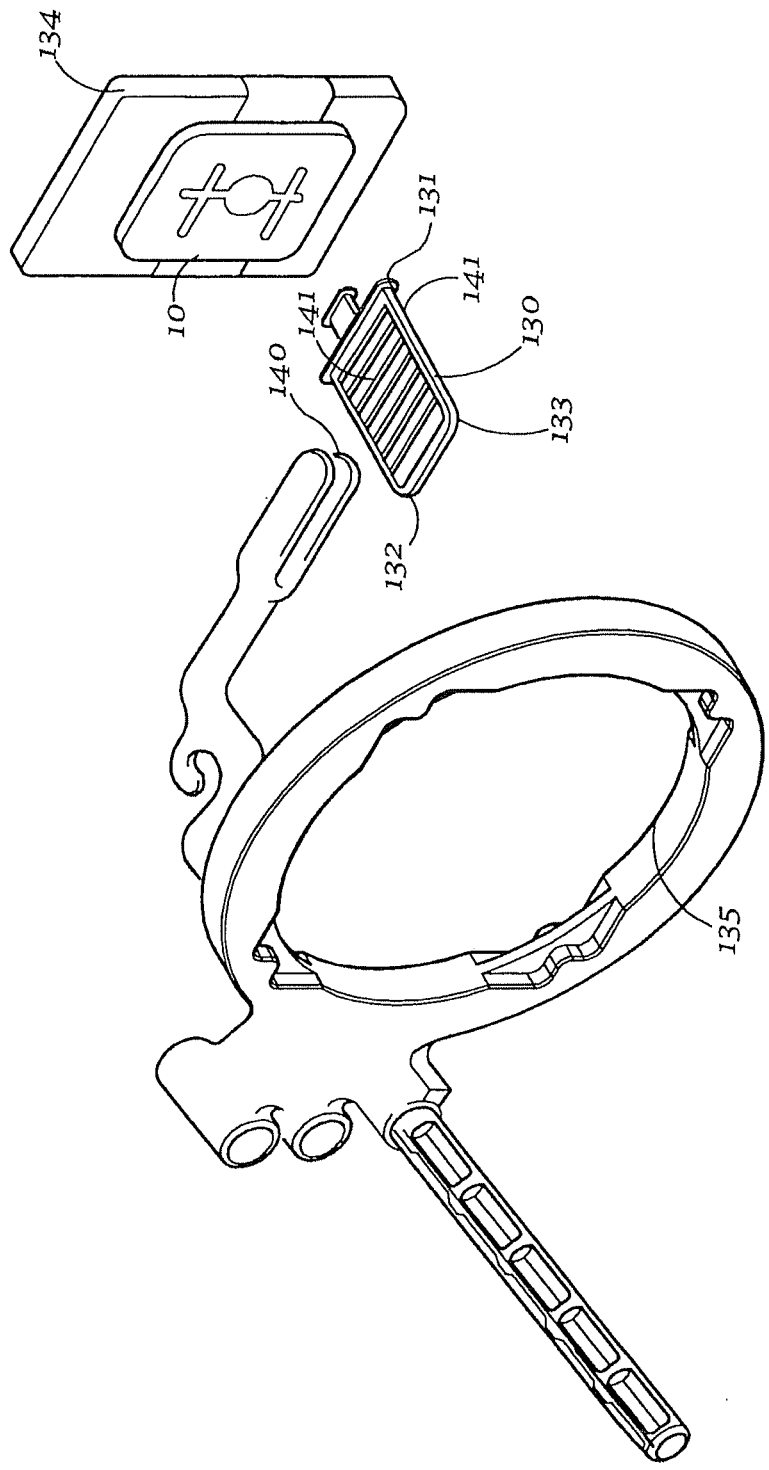
FIG. 14 is a perspective view of an exemplary aiming ring and image media receptor shown in an exploded view with the media holder and bite block of the invention.
Figure 15:
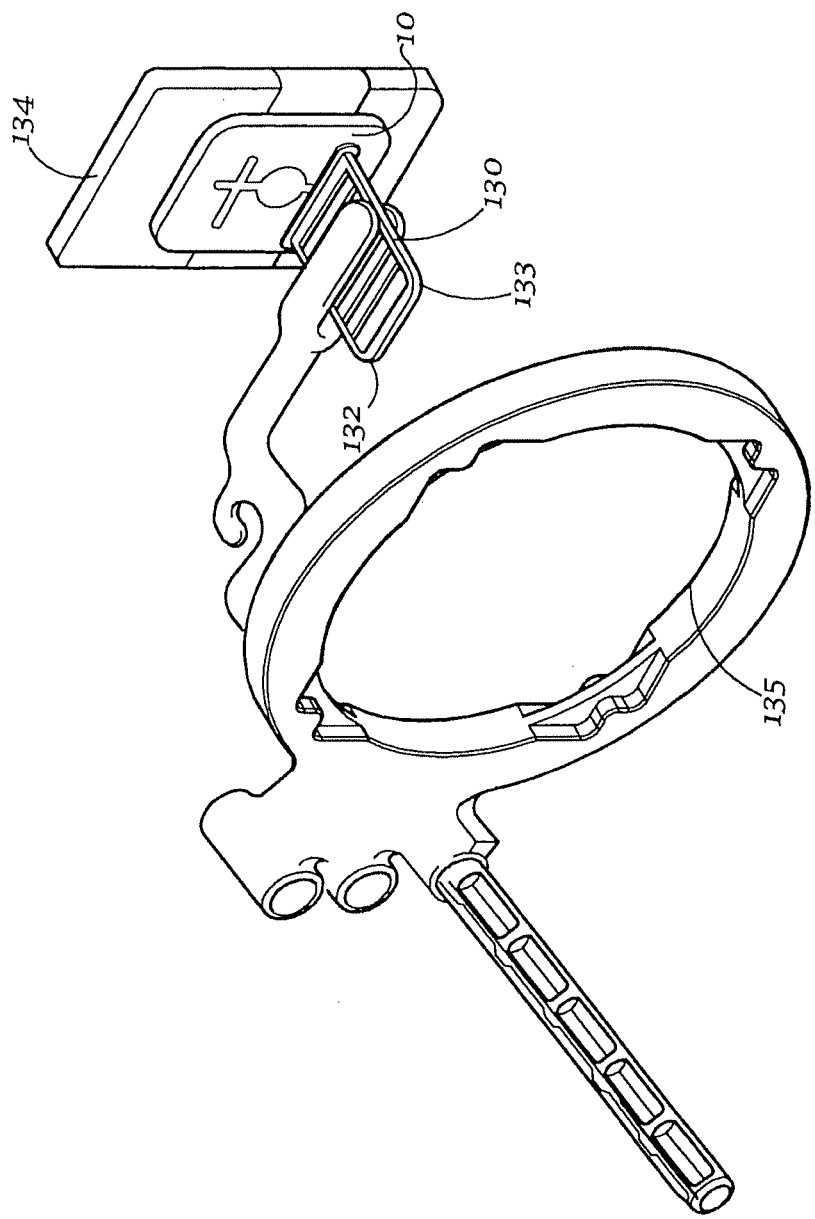
FIG. 15 is a perspective view as in FIG. 14 shown assembled.

An alternative embodiment of a bite block is designated by the number 130 on the attached drawings, namely, FIGS. 13-15. Bite block 130 is especially configured to be useful during endodontic or "root canal" procedures. As is known (but not shown) during the root canal procedure an endodontic file is used to remove the nerve from the tooth and cleanse the nerve tract within the root of the tooth. While the file is in place in the tooth, it is necessary to X-ray the tooth to assure that the endodontic file has been inserted deeply enough into the root of the tooth so that all of the nerve tract will be removed. This procedure must be done with the file in place and before it is removed.

Bite block 130 is provided with a base 131 for operative connection with inventive holder 10 in the manner described above, and is provided with a first and second bite arms 132 and 133. Arms 132 and 133 are preferably arranged in a spaced, parallel and opposing relation as shown on the drawings. By being spaced, there is room for an endodontic file to remain in place in the root canal during the taking of an x-ray image. It will be appreciated that base 131 allows positioning of a sensor such as exemplary sensor 134 in multiple positions in the same inventive manner as described hereinabove with respect to holder 10.

Further, it is preferred although not required that bite block 130 be provided with means for being affixed or removably affixed to an aiming ring 135. For example, ring 135 may be provided with spaced, opposing parallel grooves 140 and bite block 130 may be provided with complementary pins 141. Grooves 140 and pins 141 may be configured such that grooves 140 may be frictionally fit over pins 141 by sliding. The friction between grooves 140 and pins 141 may be sufficient to hold ring 135 in place as needed. It will be appreciated that any means of affixing bite block 130 to ring 135 is within the scope of the invention.

Figure 16:
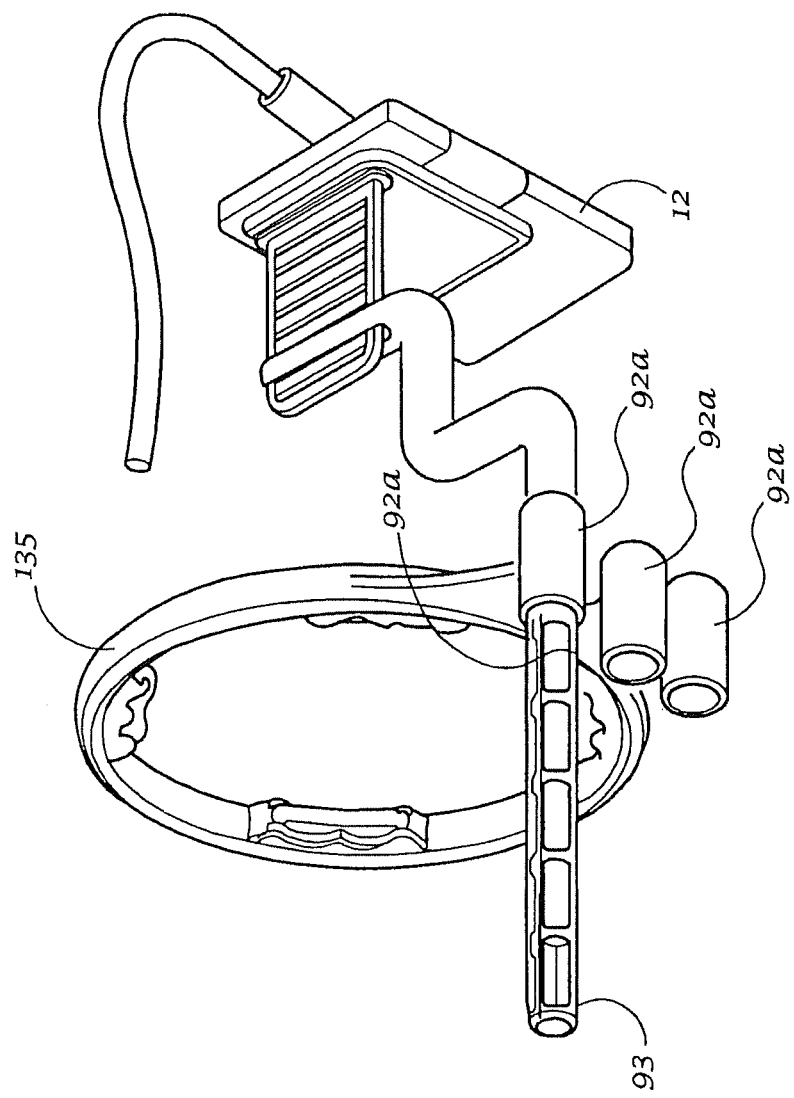
FIG. 16 is a perspective view of an alternative embodiment of the present invention, shown with an exemplary dental x-ray sensor for environmental purposes.
Figure 17:
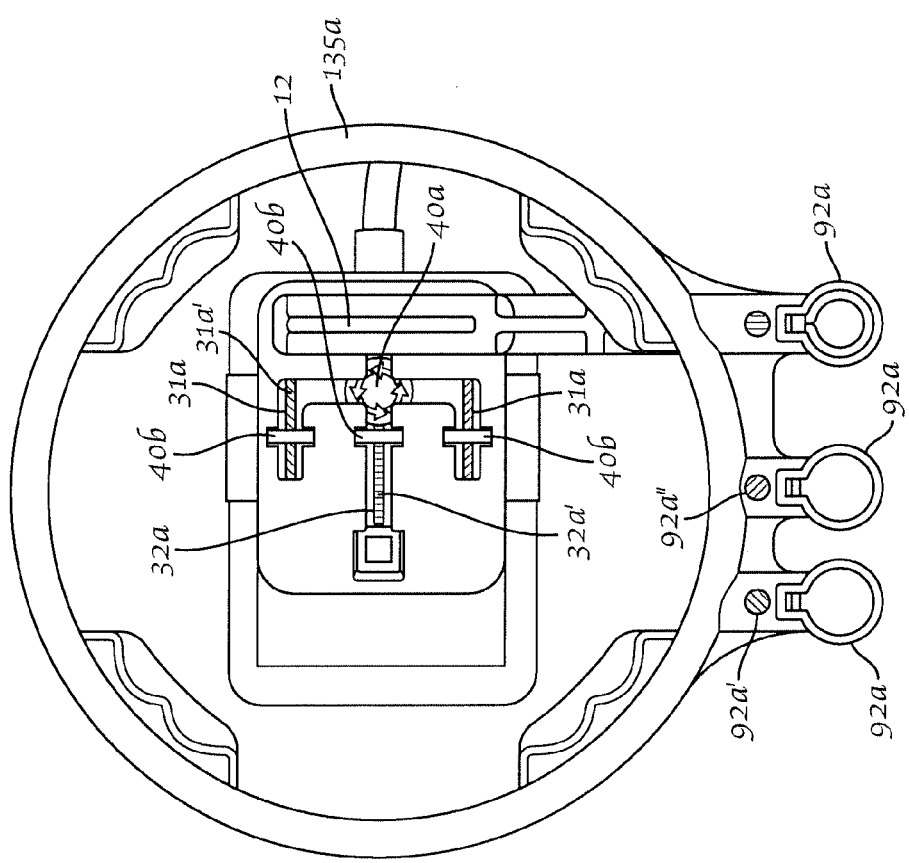
FIG. 17 is a side, plan view of the alternative embodiment shown in FIG. 16
Figure 18:
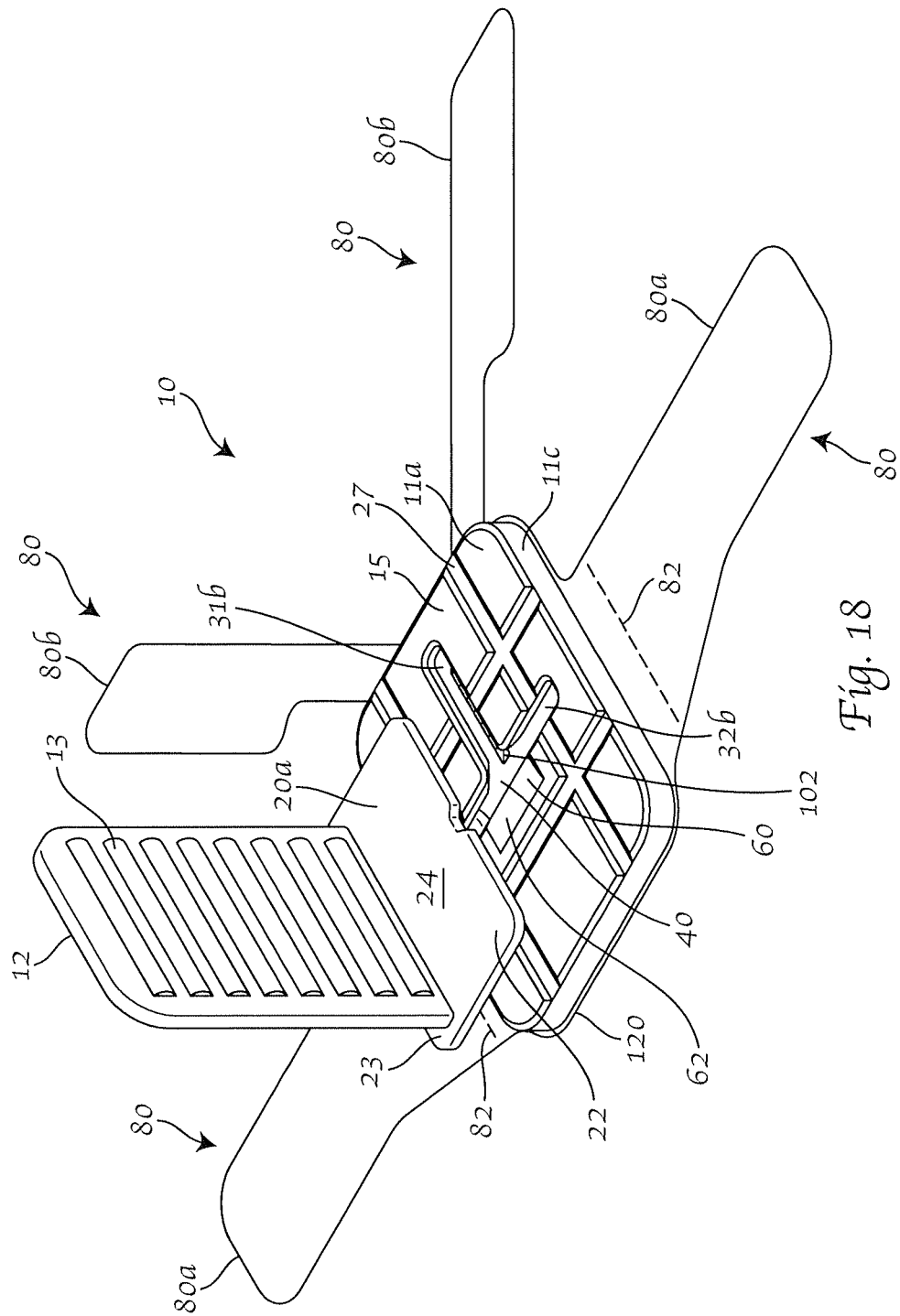
FIG. 18 is a perspective view of an alternative embodiment of the present invention.
Figure 19:
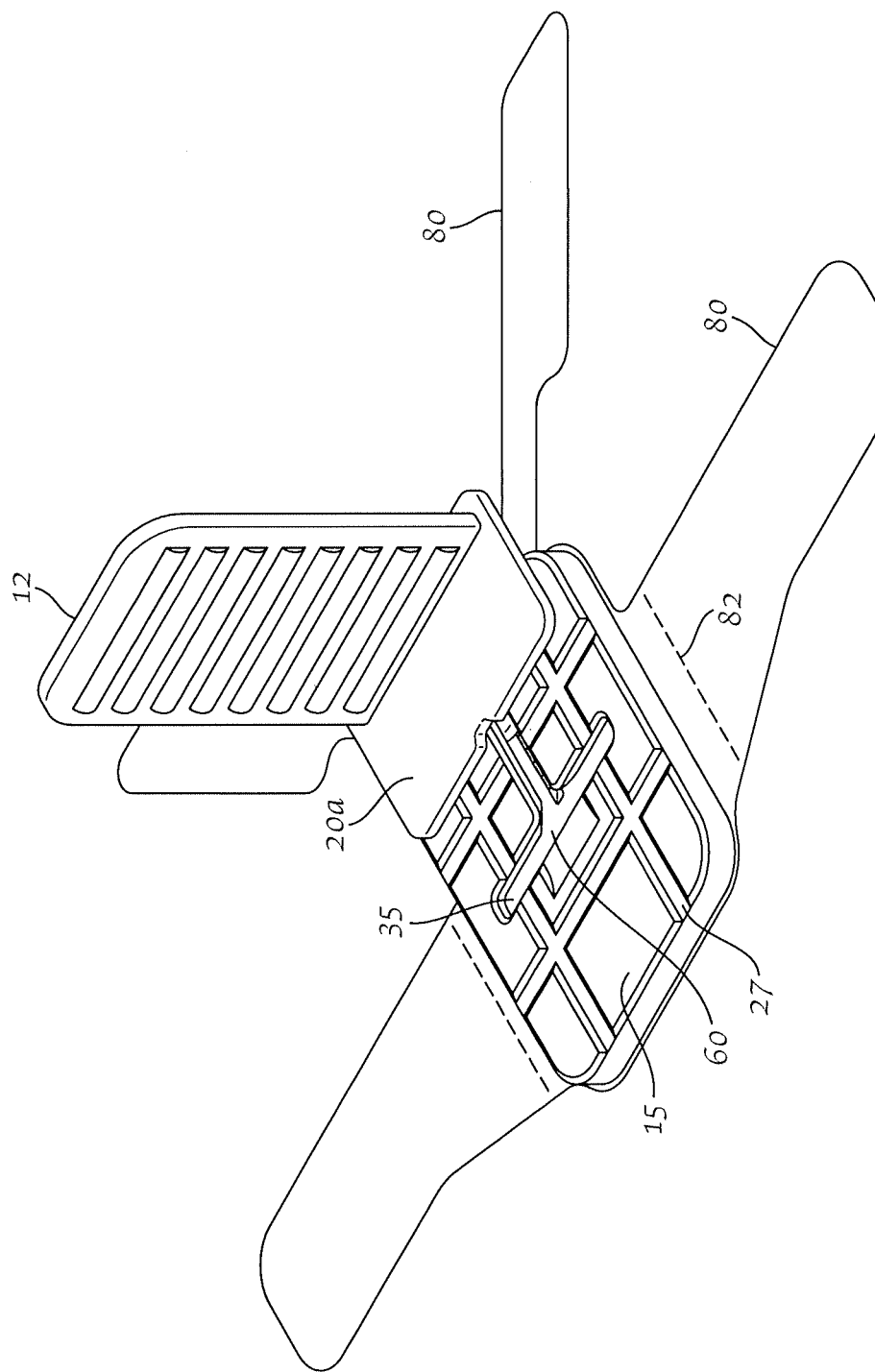
FIG. 19 is a perspective view of the alternative embodiment shown in FIG. 18 with the bite block component shown in an alternate position.

An alternative configuration of channels are shown as channels 31a and 32a, and an alternative intersection is shown as intersection 40a in drawings FIGS. 16 and 17. In addition, intermediate rotation permitting open areas 40b are provided at a variety of points such that bite block 12 may be rotated at a point away from intersection 40a, if desired. In addition, aiming ring 135a similar to aiming ring 135 may be provided with a plurality of supports 92a each capable of supporting arm 93. In a preferred configuration, each support 92a holds arm 93 in a preselected position facilitating the taking of a particular dental x-ray image. Further still, indicia 31a' and 32a' within channels 31a and 32a respectively, and indicia 40a' in intersection 40a correspond to indicia located upon, adjacent or otherwise affiliated with a given support 92a. For example, indicia 31a' might be a color such as the color yellow, which corresponds to yellow color indicia 92a' positioned close too and hence affiliated with or otherwise indicating support 92a. When bite block 12 is positioned within channel 32a, as such was described above, the user will place arm 93 within support 92a knowing that the assembled elements are now in the proper position for a given x-ray imaging procedure. As a further example, indicia 31a' and associated support 92a indicated to the user by indicia 92a', might be useful for the taking of a posterior image. Indicia 32a' and associated support 92a" might be a second color such as red, and may indicate the proper position for the taking of a bitewing image. Other positions may be proper for the taking of an anterior image, and the like and for example, the setup depicted in FIG. 16 happens to be useful for the taking of an anterior x-ray image. Of course, any indicia such as colors, numbers, verbiage, marks, scribes, bumps, voids, physical structures or the like applied in any manner are within the scope of the invention.

It will be appreciated therefore, that an image media holder 10 as described is capable of holding image media of different designs, shapes and configuration. The inventive image media holder is also capable of allowing the user to take dental x-rays in more than one position. All of these different uses can be accomplished with one image media holder according to the invention. The preferred embodiments for carrying out the invention have been described herein and shown on the attached drawings without attempting to show all variations that fall within the scope thereof. Therefore, the scope of the invention will be determined only by the attached claims.

What is claimed is:

1. A dental x-ray image media holder comprising
a backing plate affixed to a bite block, the backing plate including:
  a least one channel for receiving a post affixed to the bite block, such that the bite block can be selectively moved within the channels to orient the bite block in a predetermined position relative to the backing plate; and
  a plurality of indicia, such that at least one of the indicia is used to indicate a first position of the bite block relative to the backing plate, the first position being associated with a predetermined first dental imaging procedure; and
  a locking member configured to prevent rotational movement of the bite block along a post axis upon engagement of the locking member.

2. The dental x-ray image media holder of claim 1, wherein the locking member includes a first locking member of the backing plate and a corresponding second locking member of the bite block such that upon engagement of the first locking member and the corresponding second locking member, rotational movement of the bite block about the post axis is prevented while permitting generally parallel movement of the bite block within the channel relative to a first side of the blacking plate.

3. The dental x-ray image media holder of claim 2, further comprising a baseplate joining the post to the bite block, the baseplate extending along a first side of the baseplate so that in the first position, the bite block is positioned outward of a perimeter edge of the backing plate.

4. The dental x-ray image media holder of claim 3, wherein the baseplate includes a proximal end portion affixed to the post and a distal end affixed to the bite block, the bite block having a contact surface extending generally perpendicularly to the first side of the backing plate.

5. The dental x-ray image media holder of claim 1, wherein a plurality of straps are secured to a second side of the backing plate such that after an image media is placed into physical contact with the second side of the backing plate, the straps can be wrapped to physically impinge upon the image media thereby securing it in position relative to the backing plate, and wherein the straps include perforations for removing the backing plate after securement to the image media.

6. The dental x-ray image media holder of claim 3, wherein the post has base such that when positioned within at least one of the channels, a portion of the backing plate is received between the base and the baseplate with the post extending between and connecting the base and the baseplate.

7. The dental x-ray image media holder of claim 1, wherein the backing plate is provided with at least, two intersecting the channels, the channels include a t-shaped configuration made up of a primary channel intersecting a secondary channel at a midpoint of each the primary and secondary channels.

8. A dental x-ray image media holder comprising
a backing plate affixed to a bite block, the backing plate including:
  a first side;
  a perimeter edge extending along the perimeter of the first side;
  at least one channel extending at least partially through the first side of the backing plate for receiving a post affixed to the bite block, such that the bite block can be selectively moved within the channel to orient the bite block in a predetermined position relative to the backing plate; and
  a plurality of indicia, such that at least one of the indicia is used to indicate a first position of the bite block relative to the backing plate, the first position being associated with a predetermined first dental imaging procedure; and
a baseplate joining the post to the bite block, the baseplate extending along the first side of the baseplate so that in the first position, the bite block is positioned outward of the perimeter edge of the backing plate.

9. The dental x-ray image media holder of claim 8, wherein the baseplate includes a proximal end portion affixed to the post and a distal end affixed to the bite block, the bite block having a contact surface extending generally perpendicularly to the first side of the backing plate.

10. The dental x-ray image media holder of claim 9, further comprising a locking member configured to prevent rotational movement of the bite block along a post axis upon engagement of the locking member.

11. The dental x-ray image media holder of claim 10, wherein the locking member includes a first locking member having at least one groove and a corresponding second locking member having at least one rib, such that upon engagement of the rib within the groove, rotational movement of the bite block along the post axis is prevented.

12. The dental x-ray image media holder of claim 10, wherein the backing plate includes a first locking member and the baseplate includes a corresponding second locking member such that upon engagement of the first locking member and the corresponding second locking member, rotational movement of the bite block about the post axis is prevented while permitting generally parallel movement of the bite block within the channel relative to the first side of the blacking plate.

13. The dental x-ray image media holder of claim 8, wherein the backing plate is provided with at least two intersecting the channels, the channels include a t-shaped configuration made up of a primary channel intersecting a secondary channel at a midpoint of each the primary and secondary channels.

14. The dental x-ray image media holder of claim 13, wherein a plurality of straps are secured to a second side of the backing plate such that after an image media is placed into physical contact with the second side of the backing plate, the strap can be wrapped to physically impinge upon the image media thereby securing it in position relative to the backing plate.

15. A dental x-ray image media holder comprising
a backing plate affixed to a bite block, the backing plate including:
  a first side;
  a second side;
  a perimeter edge extending between the first side and the second side along the perimeter of the backing plate;
  a plurality of channels extending at least partially through the first side of the backing plate for receiving a post affixed to the bite block, such that the bite block can be selectively moved within the channels to orient the bite block in a predetermined position relative to the backing plate; and
  a plurality of indicia, such that a first indicia is used to indicate a first position of the bite block relative to the backing plate, the first position being associated with a predetermined first dental imaging procedure, and a second indicia is used to indicate a second position of the bite block relative to the backing plate, the second position being associated with a predetermined second dental imaging procedure; and
  a first locking member; and
a baseplate joining the post to the bite block, the baseplate having a corresponding second locking member for engaging the first locking member of the backing plate so that upon engagement, rotational movement of the bite block about a post axis is prevented.

16. The dental x-ray image media holder of claim 15, wherein the first locking member includes at least one longitudinally extending groove and at least one transversely extending groove along the first side of the backing plate and the corresponding second locking member includes at least one rib such that upon engagement of the first locking member and the corresponding locking member, the at least one rib is received within at least one of the at least one longitudinally extending groove and the at least one transversely extending groove.

17. The dental x-ray image media holder of claim 16, wherein the baseplate extends along the first side of the baseplate so that in the first position, the bite block is positioned outward of the perimeter edge of the backing plate.

18. The dental x-ray image media holder of claim 17, wherein the baseplate includes a proximal end portion affixed to the post and a distal end affixed to the bite block, the bite block having a contact surface extending generally perpendicularly to the first side of the backing plate.

19. The dental x-ray image media holder of claim 18, wherein the post has base such that when positioned within at least one of the channels, a portion of the backing plate is received between the base and the baseplate with the post extending between and connecting the base and the baseplate.

20. The dental x-ray image media holder of claim 19, wherein the backing plate is provided with at least two intersecting the channels, the channels include a t-shaped configuration made up of a primary channel intersecting a secondary channel at a midpoint of each the primary and secondary channels.

* * * * *